United States Patent [19]

Green et al.

[11] Patent Number: 5,383,881
[45] Date of Patent: Jan. 24, 1995

[54] SAFETY DEVICE FOR USE WITH ENDOSCOPIC INSTRUMENTATION

[75] Inventors: David T. Green, Westport; Henry Bolanos, East Norwalk, both of Conn.; Wayne P. Young, Brewster, N.Y.; Richard A. McGarry; Lisa W. Heaton, both of Norwalk, Conn.; Keith Ratcliff, Sandy Hook, Conn.

[73] Assignee: United States Surgical Corporation, Norwalk, Conn.

[21] Appl. No.: 125,519

[22] Filed: Sep. 22, 1993

Related U.S. Application Data

[60] Continuation of Ser. No. 939,029, Sep. 2, 1992, abandoned, which is a continuation of Ser. No. 794,492, Nov. 19, 1991, abandoned, which is a division of Ser. No. 530,652, May 30, 1990, Pat. No. 5,084,057, which is a continuation-in-part of Ser. No. 381,265, Jul. 18, 1989, Pat. No. 5,100,420, which is a continuation-in-part of Ser. No. 479,375, Feb. 13, 1990, Pat. No. 5,129,885.

[51] Int. Cl.[6] .............................................. A61B 17/04
[52] U.S. Cl. ...................................... 606/143; 606/142
[58] Field of Search ...................... 227/19, 175–180; 128/4–7; 604/165; 606/142–143, 19, 175–180

[56] References Cited

U.S. PATENT DOCUMENTS

| | | |
|---|---|---|
| D. 276,650 | 12/1984 | Green et al. . |
| 1,213,001 | 1/1917 | Phillips . |
| 1,880,551 | 10/1932 | Wappler .................. 128/7 |
| 2,008,367 | 7/1935 | Rhinevault . |
| 2,584,619 | 2/1952 | Rubens et al. .......... 128/5 |
| 2,741,248 | 4/1956 | Woodhall . |
| 2,968,041 | 1/1961 | Skold . |
| 3,585,985 | 6/1971 | Gould . |
| 3,603,310 | 9/1971 | Mottin et al. . |
| 3,631,707 | 1/1972 | Miller . |
| 3,777,538 | 12/1973 | Weatherly et al. . |
| 3,834,392 | 9/1974 | Lampman et al. . |
| 3,848,773 | 11/1974 | Adler et al. . |
| 3,856,016 | 12/1974 | Davis . |
| 3,870,048 | 3/1975 | Yoon . |
| 3,882,854 | 5/1975 | Hulka et al. . |
| 3,954,108 | 5/1976 | Davis . |
| 3,955,581 | 5/1976 | Spasiano et al. . |
| 3,989,049 | 11/1976 | Yoon . |
| 4,027,510 | 6/1977 | Hiltebrandt . |
| 4,038,987 | 8/1977 | Komiya . |
| 4,064,881 | 12/1977 | Meredith . |
| 4,084,594 | 4/1978 | Mosior . |
| 4,085,743 | 4/1978 | Yoon . |
| 4,101,063 | 7/1978 | Kapitanov et al. . |
| 4,103,680 | 8/1978 | Yoon . |

(List continued on next page.)

FOREIGN PATENT DOCUMENTS

| | | |
|---|---|---|
| 0113520 | 7/1984 | European Pat. Off. . |
| 0406724 | 1/1991 | European Pat. Off. . |
| 0409569 | 1/1991 | European Pat. Off. . |
| 2330182 | 1/1975 | Germany . |
| 2546696 | 4/1976 | Germany . |
| 3802651 | 8/1989 | Germany . |
| 49-29110 | 3/1974 | Japan . |
| 2054384 | 7/1979 | United Kingdom . |
| 1093329 | 5/1984 | U.S.S.R. . |
| 8910094 | 11/1989 | WIPO . |
| 9003763 | 4/1990 | WIPO . |

OTHER PUBLICATIONS

Richard Wolf Instruction Manual, "Laparoscopic Sterilization with Spring Clips," by Jaroslav F. Hulka, M.D.
Information Booklet for Auto Suture ® Premium Surgiclip ™ Titanium Disposable Automatic Clip Appliers.

(List continued on next page.)

*Primary Examiner*—Stephen C. Pellegrino
*Assistant Examiner*—Gary Jackson

[57] ABSTRACT

A safety device is provided for use with endoscopic instrumentation, particularly and endoscopic clip applier. The device includes a collar which is adapted to be disposed on the elongated shaft of the endoscopic instrument. A release means is provided as part of the trocar guide sleeve which is adapted to contact the collar and release it from engagement with the elongated shaft.

1 Claim, 15 Drawing Sheets

U.S. PATENT DOCUMENTS

| | | | |
|---|---|---|---|
| 4,152,920 | 5/1979 | Green . | |
| 4,166,466 | 9/1979 | Jarvik . | |
| 4,169,476 | 10/1979 | Hiltebrandt . | |
| 4,185,762 | 1/1980 | Froehlich . | |
| 4,188,942 | 2/1980 | Fehlberg | 128/6 |
| 4,188,953 | 2/1980 | Klieman et al. . | |
| 4,196,836 | 4/1980 | Becht . | |
| 4,226,239 | 10/1980 | Polk et al. . | |
| 4,226,242 | 10/1980 | Jarvik . | |
| 4,228,895 | 10/1980 | Larkin . | |
| 4,230,116 | 10/1980 | Watson . | |
| 4,240,411 | 12/1980 | Hosono . | |
| 4,242,902 | 1/1981 | Green . | |
| 4,243,034 | 1/1981 | Brandt . | |
| 4,246,903 | 1/1981 | Larkin . | |
| 4,254,762 | 3/1981 | Yoon | 128/4 |
| 4,257,419 | 3/1981 | Goltner et al. . | |
| 4,273,129 | 6/1981 | Boebel . | |
| 4,296,751 | 10/1981 | Blake, III et al. . | |
| 4,299,224 | 11/1981 | Nailes . | |
| 4,316,468 | 2/1982 | Klieman et al. . | |
| 4,325,376 | 4/1982 | Klieman et al. . | |
| 4,325,377 | 4/1982 | Boebel . | |
| 4,335,928 | 6/1982 | Barrett et al. . | |
| 4,338,947 | 7/1982 | Williams . | |
| 4,367,746 | 1/1983 | Derechinsky . | |
| 4,372,316 | 2/1983 | Blake, III et al. . | |
| 4,374,523 | 2/1983 | Yoon . | |
| 4,393,883 | 7/1983 | Smyth et al. . | |
| 4,412,539 | 11/1983 | Jarvik . | |
| 4,425,915 | 1/1984 | Ivanov . | |
| 4,430,997 | 2/1984 | DiGiovanni et al. . | |
| 4,440,170 | 4/1984 | Golden et al. . | |
| 4,450,839 | 5/1984 | Transue . | |
| 4,452,357 | 6/1984 | Klieman et al. . | |
| 4,452,376 | 6/1984 | Klieman et al. . | |
| 4,471,780 | 9/1984 | Menges et al. . | |
| 4,479,489 | 10/1984 | Tucci . | |
| 4,480,641 | 11/1984 | Failla et al. . | |
| 4,481,952 | 11/1984 | Pawelec . | |
| 4,492,232 | 1/1985 | Green . | |
| 4,505,414 | 3/1985 | Filipi . | |
| 4,509,518 | 4/1985 | McGarry et al. . | |
| 4,512,345 | 4/1985 | Green . | |
| 4,522,207 | 6/1985 | Klieman et al. . | |
| 4,532,925 | 8/1985 | Blake, III . | |
| 4,534,351 | 8/1985 | Rothfuss et al. . | |
| 4,549,544 | 10/1985 | Favaron . | |
| 4,550,715 | 11/1985 | Santangelo et al. | 128/4 |
| 4,557,263 | 12/1985 | Green . | |
| 4,558,706 | 12/1985 | Nakada et al. . | |
| 4,562,839 | 1/1986 | Blake, III et al. . | |
| 4,572,183 | 2/1986 | Juska . | |
| 4,573,981 | 3/1986 | McFarlane . | |
| 4,576,166 | 3/1986 | Montgomery et al. . | |
| 4,589,421 | 5/1986 | Ullman . | |
| 4,598,711 | 7/1986 | Deniega . | |
| 4,601,710 | 7/1986 | Moll | 604/165 |
| 4,609,370 | 9/1986 | Morrison | 604/165 |
| 4,611,595 | 9/1986 | Klieman et al. . | |
| 4,613,329 | 9/1986 | Bodicky . | |
| 4,616,650 | 10/1986 | Green et al. . | |
| 4,624,254 | 11/1986 | McGarry et al. . | |
| 4,633,882 | 1/1987 | Matsuo et al. . | |
| 4,646,740 | 3/1987 | Peters et al. . | |
| 4,649,904 | 3/1987 | Krauter et al. . | |
| 4,654,030 | 3/1987 | Moll . | |
| 4,662,373 | 5/1987 | Montgomery et al. . | |
| 4,662,374 | 5/1987 | Blake, III . | |
| 4,674,501 | 6/1987 | Greenberg . | |
| 4,674,504 | 6/1987 | Klieman et al. . | |
| 4,682,491 | 7/1987 | Pickard . | |
| 4,691,853 | 9/1987 | Storace . | |
| 4,700,694 | 10/1987 | Shishido . | |
| 4,712,549 | 12/1987 | Peters et al. . | |
| 4,735,614 | 4/1988 | Yapp et al. | 604/165 |
| 4,759,364 | 7/1988 | Boebel . | |
| 4,784,137 | 11/1988 | Kulik . | |
| 4,841,888 | 6/1989 | Mills et al. . | |
| 4,850,350 | 7/1989 | Jackson . | |
| 4,850,355 | 7/1989 | Brooks et al. . | |
| 4,858,608 | 8/1989 | McQuilkin . | |
| 4,874,364 | 10/1989 | Morris et al. . | |
| 4,900,307 | 2/1990 | Kulli . | |
| 4,919,152 | 4/1990 | Ger . | |
| 4,935,010 | 6/1990 | Cox et al. . | |
| 4,944,443 | 7/1990 | Oddsen et al. . | |
| 5,026,379 | 6/1991 | Yoon . | |
| 5,030,226 | 7/1991 | Green et al. . | |
| 5,040,715 | 8/1991 | Green et al. . | |
| 5,049,152 | 9/1991 | Simon et al. . | |
| 5,100,418 | 3/1992 | Yoon et al. . | |
| 5,104,395 | 4/1992 | Thornton et al. . | |

OTHER PUBLICATIONS

Information Booklet for Auto Suture ® Skin and Fascia Surgical Stapling Instruments and Disposable Loading Units.

"Information About Dimethyl Silicone Compounds,"

(List continued on next page.)

OTHER PUBLICATIONS

Dow Corning, 1988.

"Laparoscopic Sterilization with Electrocautery, Spring-Loaded Clips, and Silastic Bands: Technical Problems and Early Complications," *Fertility and Sterility*, vol. 27, No. 3, Mar. 1976.

"A Clip Applicator for Laparoscopic Sterilization," *Fertility and Sterility*, vol. 27, No. 9, Sep. 1976.

"Laparoscopic Sterilization with Spring-Loaded Clips: Double-Puncture Technique," *The Journal of Reproductive Medicine*, vol. 18, No. 5, May 1977.

"Laparoscopic Sterilization with the Spring-Clip: Instrumentation development and Current Clinical Experience," *American Journal of Obstetrics and Gynecology*, vol. 135, No. 8, Dec. 15, 1979.

Karl Storz Endoscopy-America Promotional Advertisement, "It's Your Choice for Tubal Sterilization," 1981.

"An Applicator for the Hulka Fallopian Tube Clip," *The American Journal of Obstetrics and Gynecology*, vol. 139, No. 6, Mar. 15, 1981.

"Metal Clip Techniques Utilizing Pistol Grip Appliers," *The American Journal of Surgery*, Feb. 1982.

"Results of Experimental Endoscopic Esophagel Varix Litigation," *The American Surgeon*, Jan. 1988.

Edward Weck & Company Promotional Advertisement, "We've Corrected Everybody's Flaws," Sep. 1986.

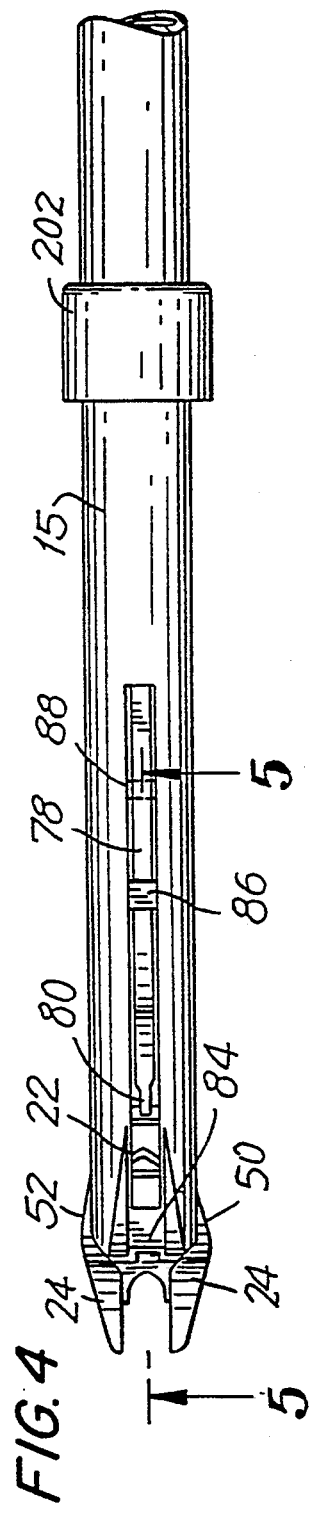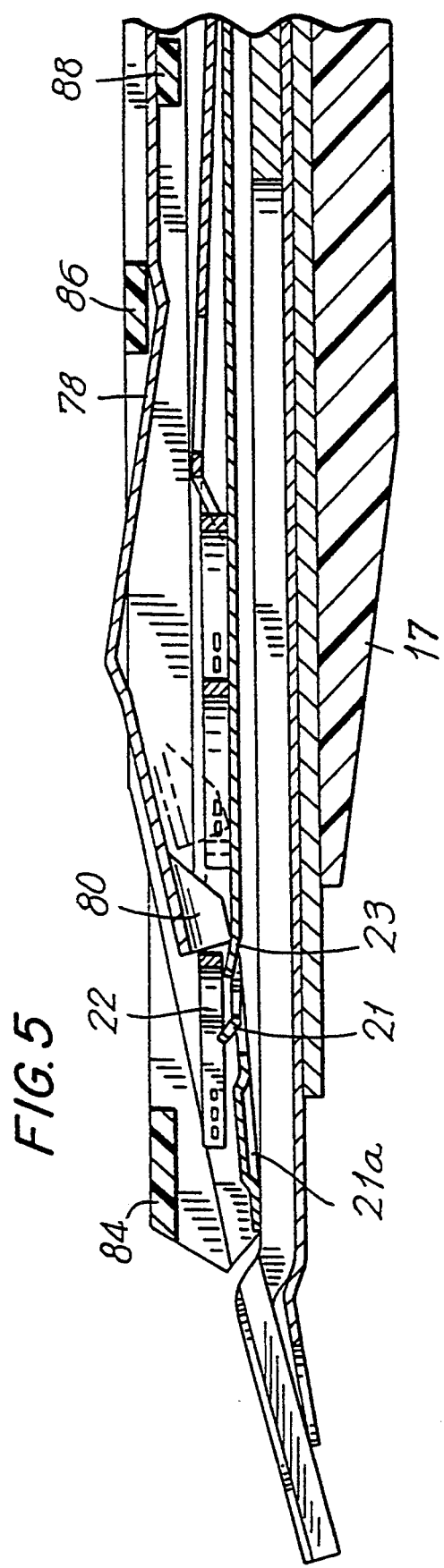

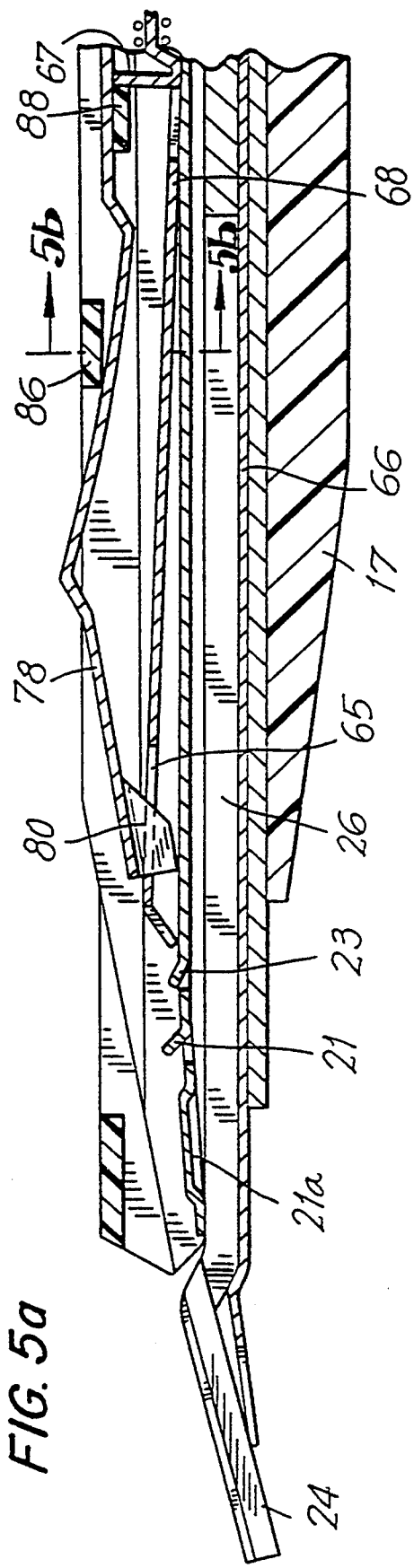
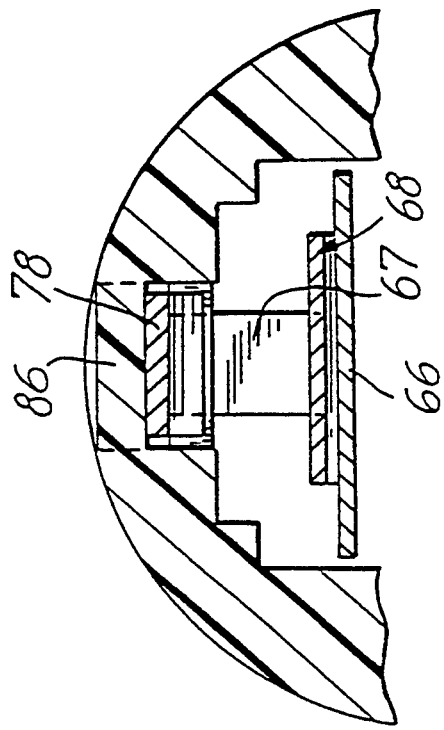
FIG. 5a
FIG. 5b

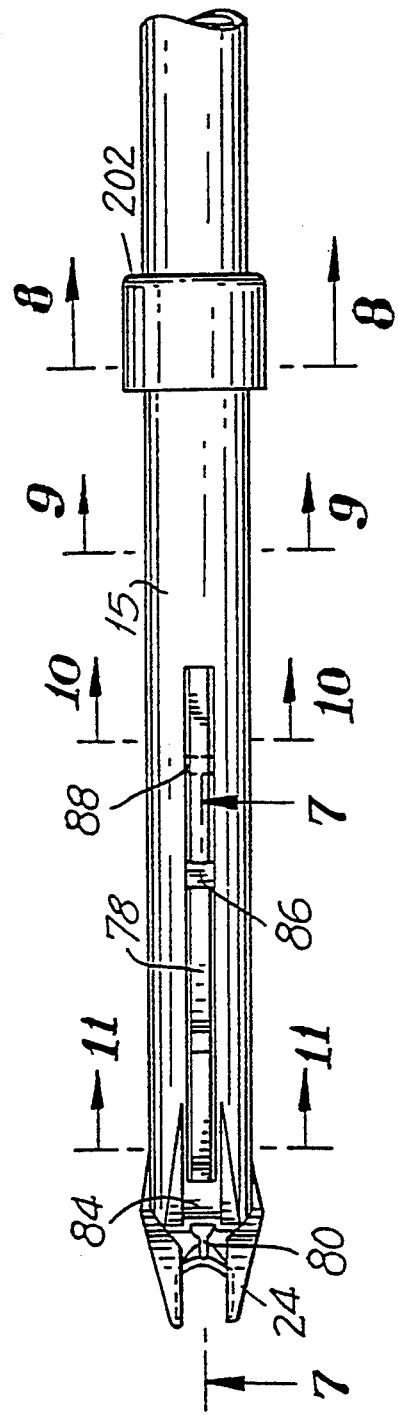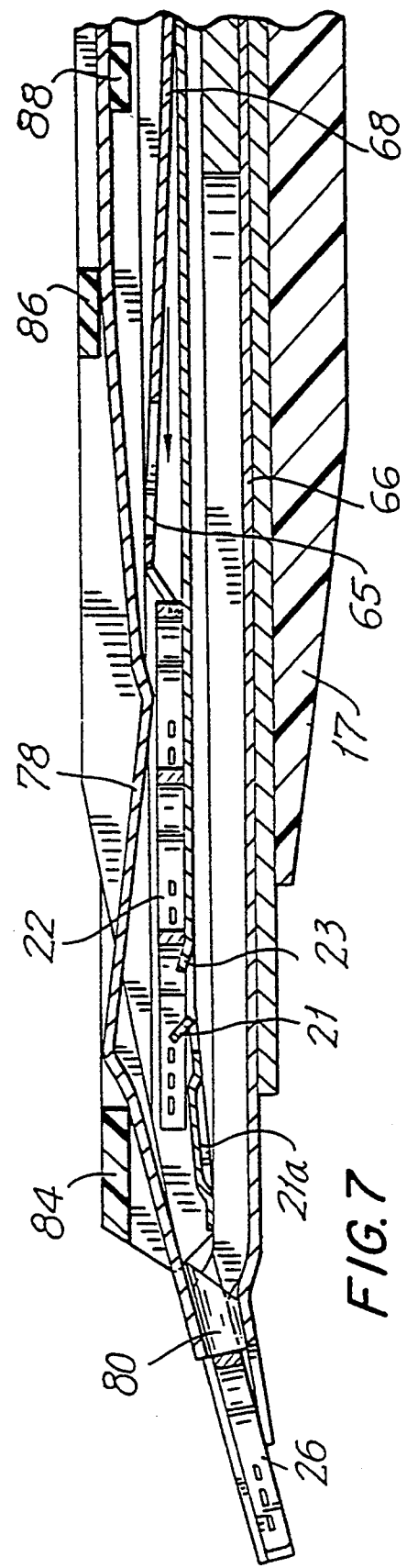

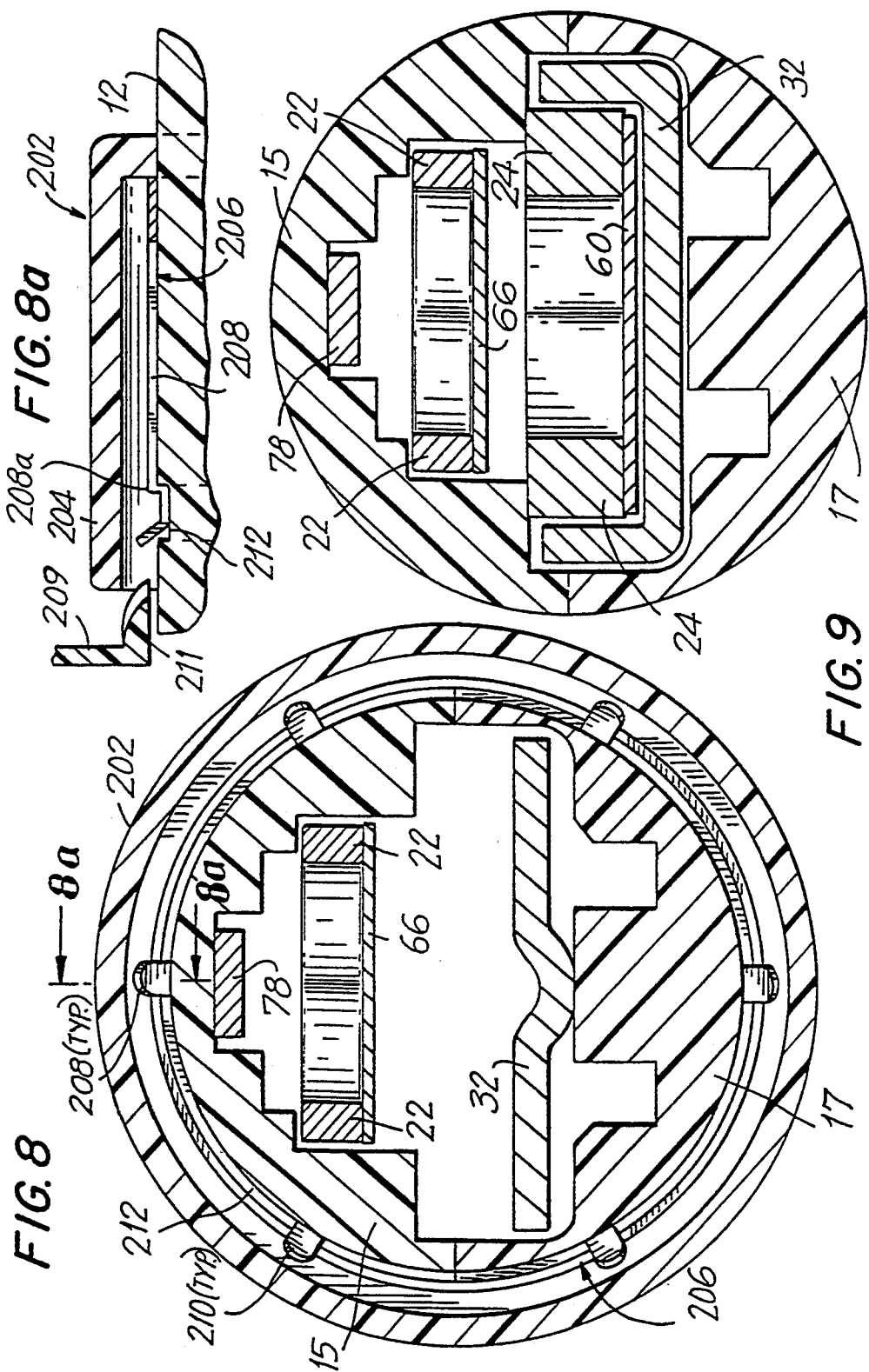

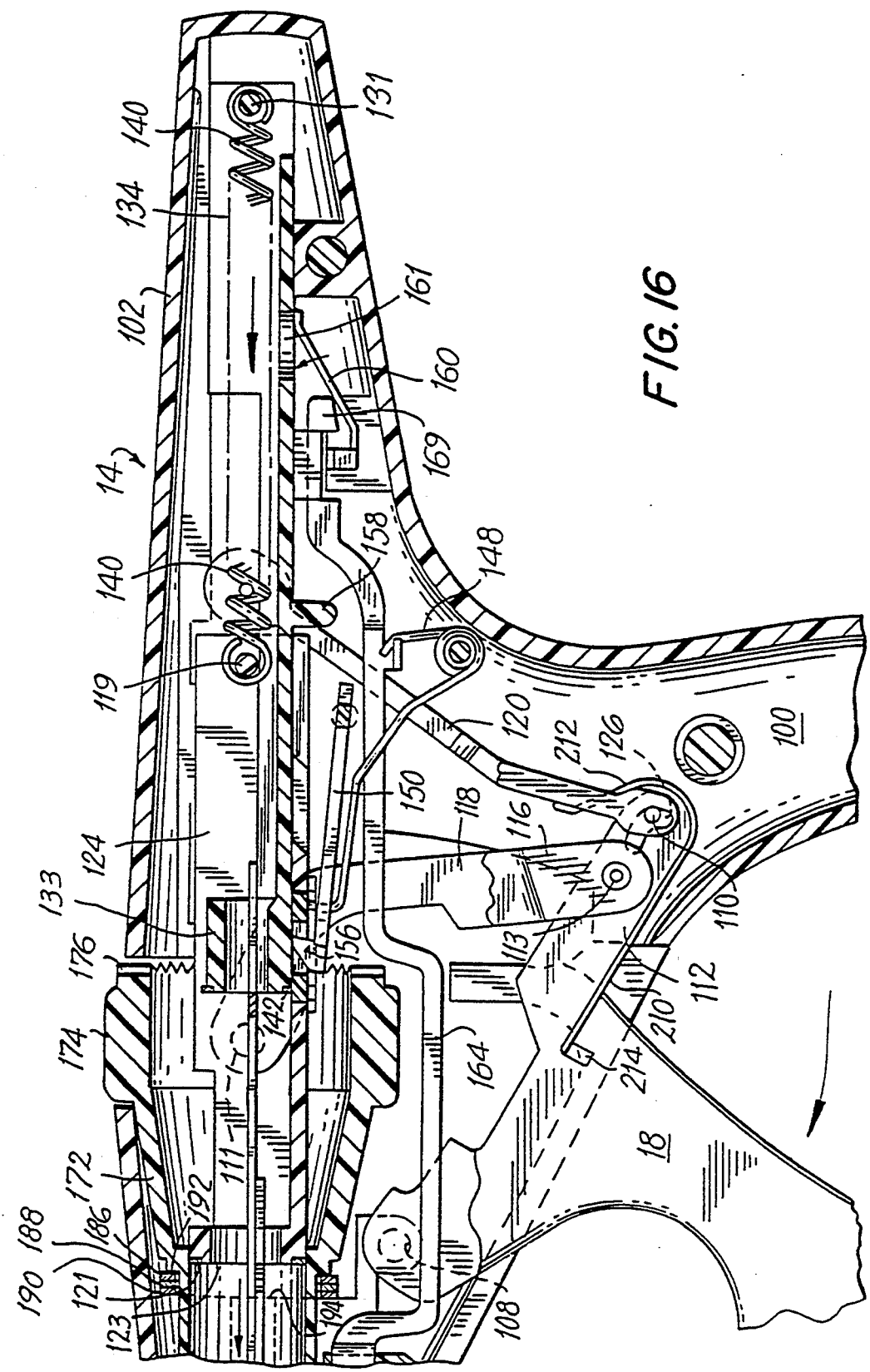

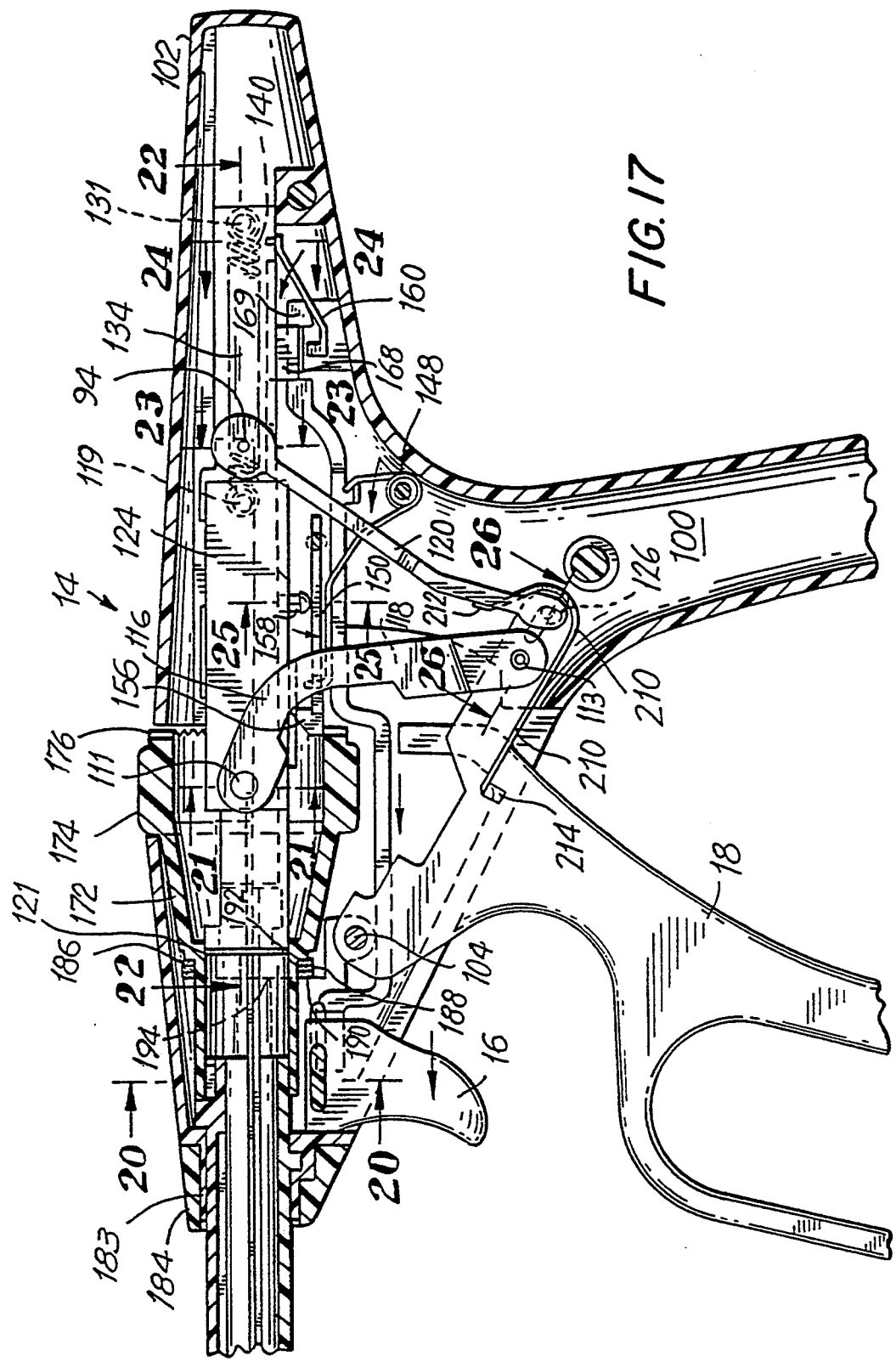

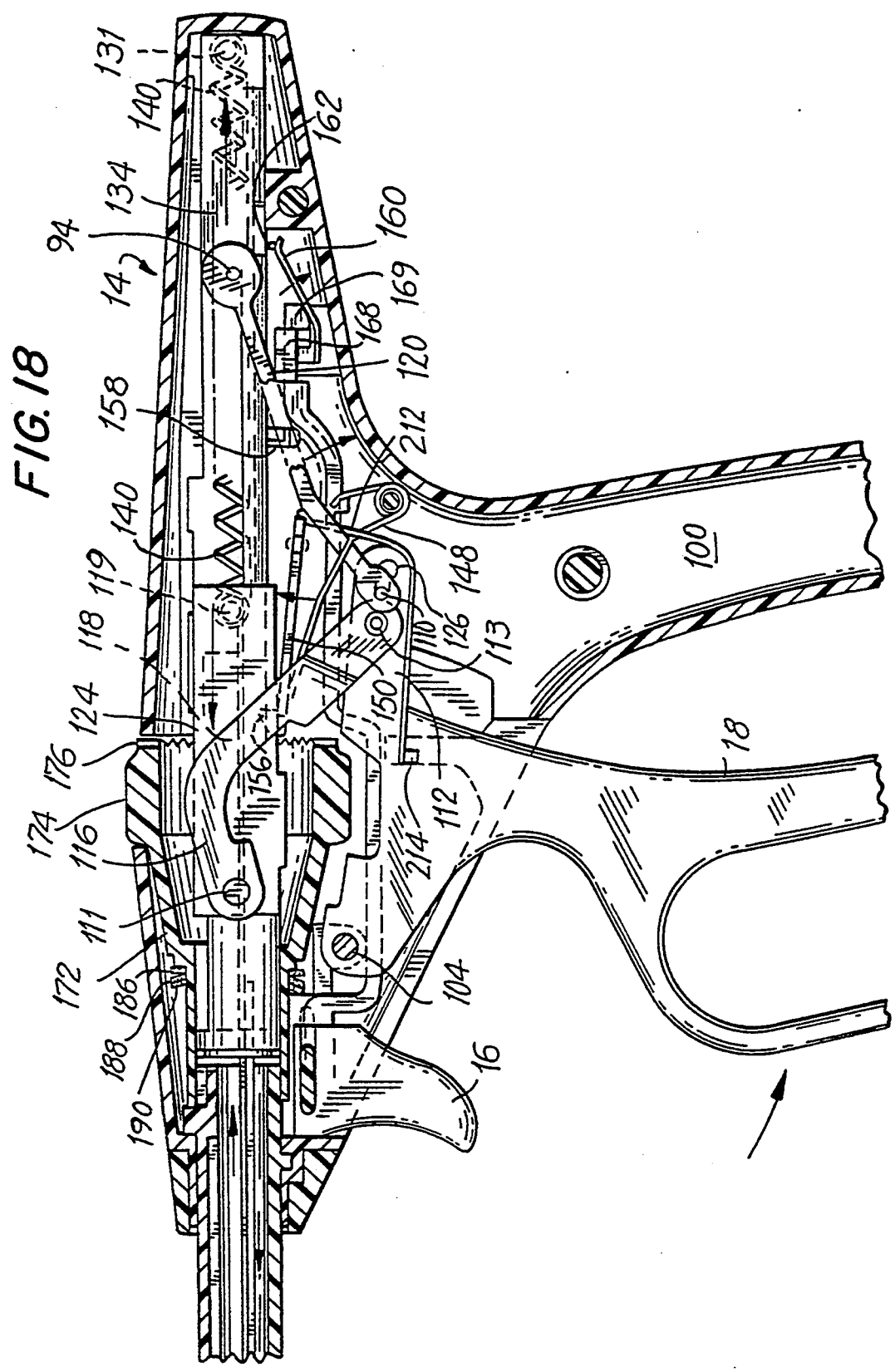

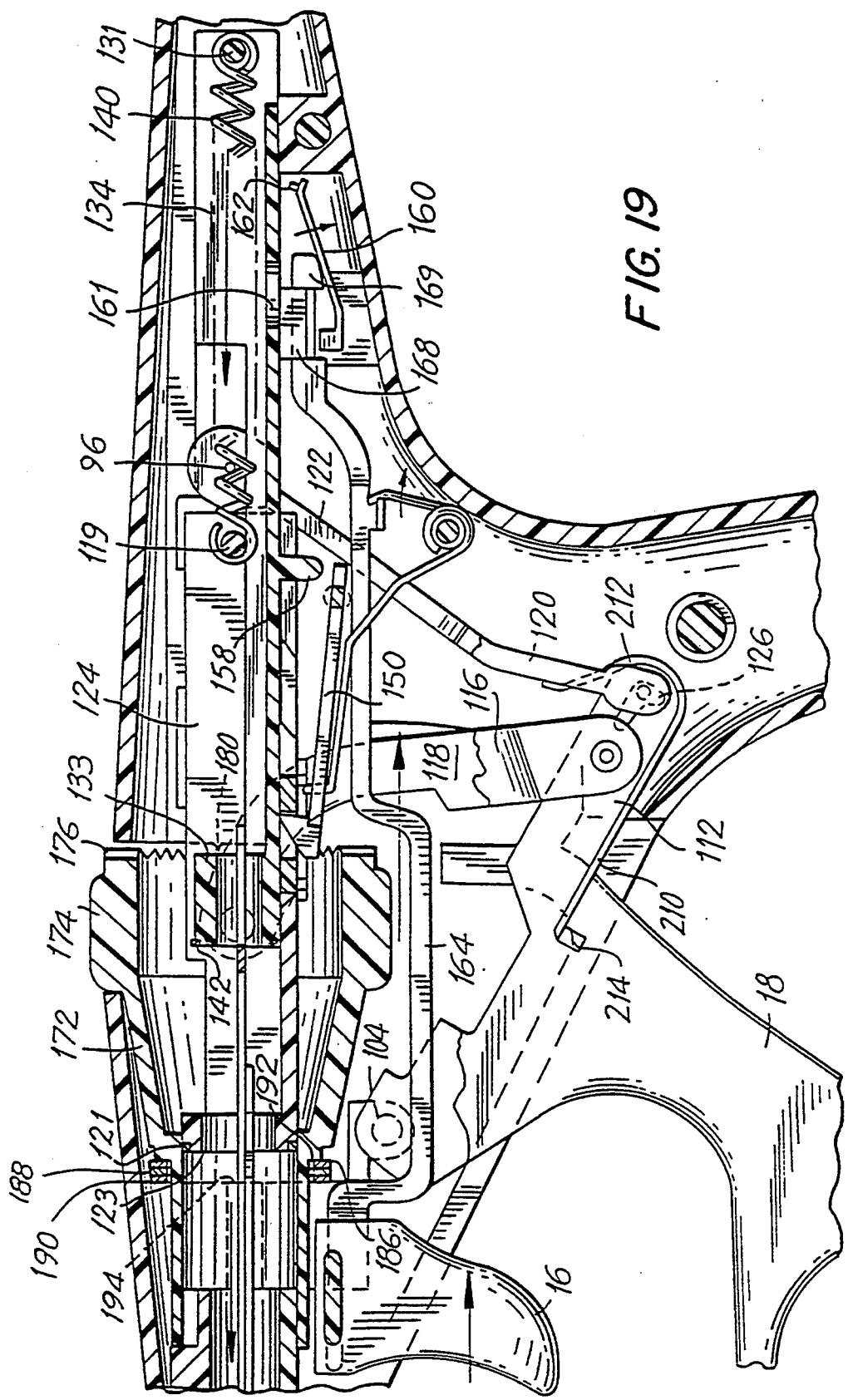

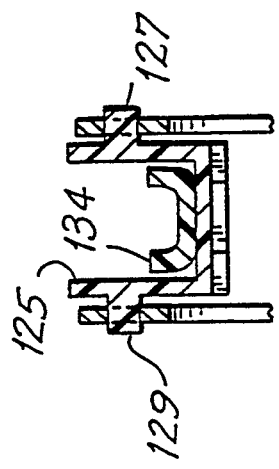
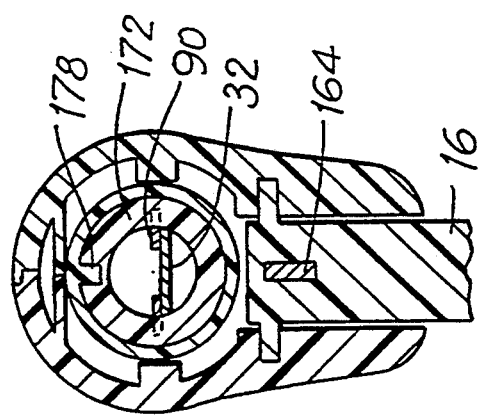
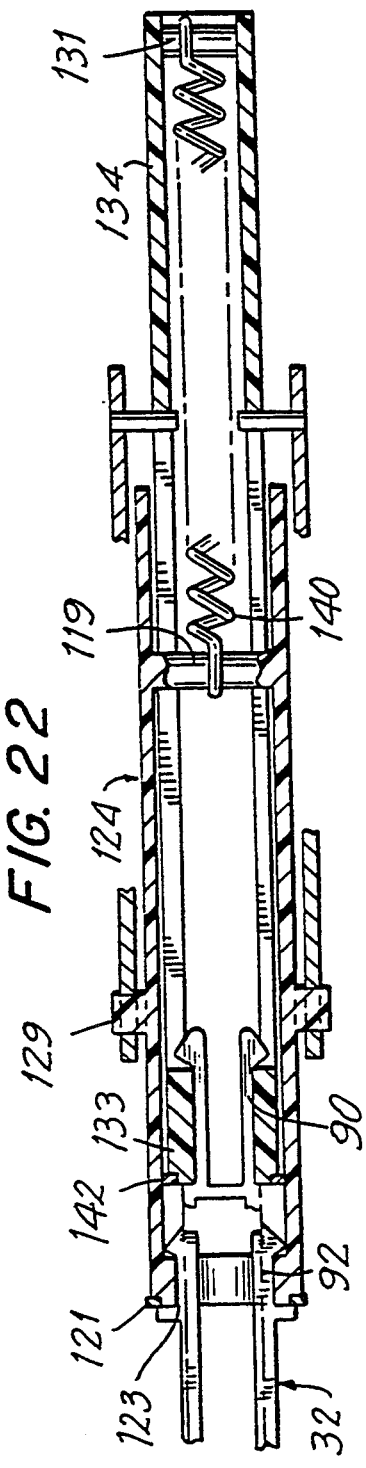

SAFETY DEVICE FOR USE WITH ENDOSCOPIC INSTRUMENTATION

CROSS REFERENCE TO RELATED APPLICATIONS

This is a continuation of Ser. No. 07,939,029 filed Sep. 2, 1992, now abandoned, which was a continuation of Ser. No. 07/794,492, filed Nov. 19, 1991, now abandoned, which was a divisional of Ser. No. 07/530,652, filed May 30, 1990, now U.S. Pat. No. 5,084,057, which was a continuation-in-part of both Ser. No. 07/381,265, filed Jul. 18, 1989, now U.S. Pat. No. 5,100,420, and Ser. No. 07/479,375, filed Feb. 13, 1990, now U.S. Pat. No. 5,129,885.

BACKGROUND OF THE INVENTION

1. Field of the Invention

This invention relates to an apparatus and method for applying surgical clips, especially hemostatic clips, to body tissue such as blood vessels. More particularly, this invention relates to a surgical clip applier which can be used in laparoscopic or endoscopic procedures for closing arteries, and a method for clipping such tissue.

2. Background of the Related Prior Art

In surgical operations it is often necessary to apply hemostatic clips to blood vessels, and apparatus for applying clips are known in the art. See, for example, U.S. Pat. Nos. 4,616,650 and 4,624,254, both of which are hereby incorporated by reference, which disclose a surgical clip applying apparatus having a pair of ring-like handles. The handles are squeezed to force jaws to move distally relative to the apparatus where they are forced together by a pair of inclined surfaces. A surgical clip between the jaws is thereby squeezed closed.

In laparoscopic procedures surgery is performed through a small incision; in endoscopic procedures surgery is performed through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues, and vessels far removed from the incision, thereby requiring that any instruments to be used in such procedures be both long and narrow.

Copending parent application Ser. No. 07/381,265, filed Jul. 18, 1989, discloses an improved apparatus for applying clips to blood vessels which includes a handle section and an endoscopic section which is preferable replaceable when the entire supply of clips are spent. The entire application Ser. No. 07/381,265 is herein incorporated by reference.

While this development represented a major advance in clip applicators, the present invention is directed to further improvements whereby a disposable clip applicator can function to advance and to apply clips in rapid sequence where desirable, while having the capability of becoming locked against further action after the last clip is spent. Since the preferred embodiment of the present invention contemplates a clip applier which is entirely disposable, the endoscopic section is thereby preferably permanently connected to the handle section. Furthermore, the present invention permits ease of gripping while facilitating partial or full closing of each clip without interference with the sequential advancement and closing operation of the endoscopic section.

Because endoscopic procedures are more common than laparoscopic procedures, the present invention shall be discussed in terms of endoscopic procedures and apparatus. However, use herein of terms such as "endoscopic", "endoscopically" and "endoscopic portion", among others, refer generally to instruments having elongated and relatively narrow operating portions for inserting into a cannula or a small wound in the skin and should not be construed to limit the present invention to an apparatus for applying surgical clips only in conjunction with an endoscopic tube. To the contrary, it is believed that the present invention may find use in any procedure where access is limited to a small incision, including, but not limited to laparoscopic procedures.

SUMMARY OF THE INVENTION

An apparatus is disclosed for applying surgical clips to body tissue which comprises frame means, endoscopic means connected to the frame means of generally elongated configuration and extending distally from the frame means and including means for storing a plurality of surgical clips, means for selectively advancing the clips to the distal portion of the endoscopic means for positioning adjacent the body tissue to be clipped; and means for at least partially closing each clip at least sufficient to grip the body tissue after the clip has been advanced distally to the predetermined portion of the endoscopic means.

Preferably, the disposable apparatus for applying surgical clips to body tissue comprises a frame, an elongated endoscopic section connected at the proximal end thereof to the frame and extending distally from the frame. The endoscopic section includes means for storing a plurality of surgical clips and a pair of jaws positioned at the distal portion of the endoscopic section and adapted for reception of the clips. Means is provided for sequentially advancing the clips distally for positioning within the pair of jaws to be positioned adjacent the body tissue to be clipped; and means is provided for sequentially at least partially closing the jaws about the clips to close the clips at least partially about the body tissue.

In one embodiment, a disposable apparatus is disclosed for applying Surgical clips to body tissue which comprises a frame configured and dimensioned for manual gripping, an elongated endoscopic section connected at the proximal end thereof to the frame and extending distally therefrom, the endoscopic section including means for storing a plurality of surgical clips in generally aligned relation facing the distal portion thereof, jaw means positioned at the distal end thereof and adapted for sequential reception of the clips, means for sequentially advancing the clips distally as to be positioned between the jaw means for positioning adjacent the body tissue to be clipped, and means for sequentially at least partially closing the jaw means about each clip after the clip is advanced therebetween while simultaneously repositioning the clip advancing means for distal advancement of the next clip.

Preferably, an instrument body is provided and an actuating handle mounted to the instrument body, with first transmission means for linearly transferring motion from the actuating handle to the clip advancing means and means to close the jaw means. Second transmission means is provided for linearly transferring motion from the actuating handle to the jaw closing means, and means is provided for locking the handle such that after actuating the handle to close the jaws the handle cannot be actuated unless the locking means is released. The endoscopic section is rotatable independent of the handle, with means being provided to selectively lock the endoscopic section at a predetermined angular orientation relative to the handle. Means is provided to release the lock means of the endoscopic section so as to permit rotation thereof relative to the handle.

Handle locking means comprises a first resilient catch movable in response to actuation of the handle from an unlocked position to a locked position wherein the first transmission means is advanced and locked. Release means is adapted to release the first resilient catch, the first resilient catch being returnable to the unlocked position in response to actuation of the release means. A second resilient catch is movable in response to actuation of the handle from an unlocked position to a locked position wherein it engages and locks the second transmission means. The second resilient catch is resiliently returnable to the unlocked position in response to the release of the resilient catch. The first transmission means comprises means responsive to actuation of the release means to release the second transmission means.

The jaw means preferably comprises a pair of jaws positioned in spaced relation and configured and dimensioned for reception of a surgical clip therebetween. The jaws are resiliently movable toward and away from each other in response to distal movement of a camming means from a proximal position to a distal position. The camming means comprises a channel member slidably mounted with the endoscopic section and longitudinally movable in response to actuation of the handle. The channel member having at least two distal camming surfaces for biasing the jaws into the closed position. Means for storing surgical clips comprises a track for holding a longitudinal array of surgical clips, and resilient means located proximal to the array of surgical clips for biasing the surgical clips toward the distal direction. A clip track is positioned between the jaw means and the clip follower. Means for advancing the surgical clips comprises a pusher bar for advancing the distal-most clip in the area of the pair of jaws, the pusher bar being longitudinally slidable in response to actuation of the handle, and escapement means located at the distal end of the array of clips for preventing more than one clip at a time from being advanced into the jaw means. The escapement means comprises a plurality of projections upstanding from the clip track and extending into the clip path.

The first transmission means comprises a pusher bar, and a proximal pusher tube connected to the proximal end of the pusher bar. The pusher bar is movable between a first position wherein the distal end of the pusher bar is located proximally of the surgical clip to be advanced, and a second position wherein the distal end of the pusher bar advances the surgical clip to the jaw means. The first pusher tube includes mounting means for rotatably connecting the pusher bar thereto. The mounting means of the pusher tube comprises a generally circular shaped projection dimensioned for reception and engagement of at least one cooperating projection on the pusher bar.

The second transmission means comprises a channel member positioned within the endoscopic section, a proximal channel tube connected to the proximal end portion of the channel member, and a channel tube adapted for rotatably connecting the channel member thereto. The channel member is connected to the camming means for closing the jaw means.

The jaw means preferably comprises a jaw blade fixed to the endoscopic section and having a pair of distal spaced jaws which are resiliently movable between a closed position for closing a surgical clip and an open position for reception of the surgical clip. The camming means is comprised of a channel member having camming surfaces movable from a first position proximal of the jaws, and a second distal position wherein the camming surfaces of the channel member move the jaws to the closed position. The channel member is connected at its proximal end to the channel tube.

The second transmission means comprises a channel tube having rotatable mounting means for rotatably connecting same to the camming means for closing the jaw means.

The rotatable mounting means of the channel tube comprises a circumferential projection dimensioned for engaging at least one cooperating notch in the camming means. The endoscopic section is rotatable about a longitudinal axis extending relative to the frame between a plurality of click-stop settings. Further, endoscopic section is preferably adapted to provide a gaseous seal means in the form of silicone grease. Locking means is positioned about the endoscopic section to selectively prevent entry of the endoscopic section into a tubular member in dependence upon the size of the tubular member with respect to the size of the endoscopic section. The locking means comprises a collar configured and dimensioned to be disposed about the endoscopic section. The safety locking means comprises members adapted to be releasably engaged with the endoscopic section to retain the collar in locked relation to the endoscopic section. The safety locking means comprises a plurality of resilient members adapted for releasable engagement with an outer surface portion of the endoscopic section. The members are adapted to be released by means associated with a trocar guide tube dimensioned and configured to engage and release the members when the endoscopic section is inserted into a trocar guide tube of predetermined size corresponding to the size of the endoscopic section.

The present invention also relates to a safety device for a surgical clip applying apparatus intended to be inserted into a trocar guide tube which comprises a collar member configured and dimensioned to be disposed on the elongated shaft portion of an apparatus for applying surgical clips, the apparatus having a handle section and an elongated endoscopic section, and locking means associated with the collar for releasably engaging the endoscopic section when positioned thereabout, the locking means being simultaneously released by camming means connected to the trocar guide tube.

A method is also disclosed for endoscopically applying surgical clips on apparatus having a frame adapted to be gripped by hand and an endoscopic section connected to the frame and rotatable to selected positions relative to the frame, comprising storing the clips in the endoscopic section, advancing a clip distally by clip advancing means positioned within the endoscopic section to a pair of jaws positioned at the distal end of the endoscopic section, positioning the clip adjacent body tissue to be clipped, closing the jaws about the clip while simultaneously repositioning clip advancing means to a position proximal of the next clip to be advanced, and releasably locking the clip advancing means in the position until released to advance the next clip.

BRIEF DESCRIPTION OF THE DRAWINGS

Preferred embodiments of the invention are described hereinbelow with reference to the drawings wherein:

FIG. 4 is a plan view from above, of the distal portion of the endoscopic section of the apparatus of FIG. 1;

FIG. 5 is a cross-sectional view taken along lines 5—5 of FIG. 4 illustrating the clip pusher in position to push the clip next in line to a position between the jaws of the clamp of the apparatus;

FIG. 5a is a cross-sectional view of the distal portion of the endoscopic section of the apparatus of FIG. 1, illustrating the position of the clip pusher after the last clip has been advanced into the jaws of the endoscopic section;

FIG. 5b is a cross-sectional view taken along lines 5b—5b of FIG. 5a;

FIG. 6 is a plan view from above similar to FIG. 4 of the distal portion of the endoscopic section of the apparatus with the clip pusher in the distal position with the clip shown in FIG. 5 now positioned between the jaws of the clamp;

FIG. 7 is a cross-sectional view taken along lines 7—7 of FIG. 6;

FIG. 8 is a cross-sectional view taken along lines 8—8 of FIG. 6, illustrating the safety locking feature of the invention;

FIG. 8a is a partial cross-sectional view of the safety locking feature of FIG. 8, taken along lines 8a—8a of FIG. 8;

FIG. 9 is a cross-sectional view taken along lines 9—9 of FIG. 6;

FIG. 16 is an elevational cross-sectional view of the handle of the apparatus of FIG. 1 illustrating the channel tube in the normal "at rest" position and the pusher tube in the loaded position corresponding to the position of the clip pusher in the proximal position about to push the next clip distally into the jaws;

FIG. 17 is an elevational cross-sectional view of the handle of the apparatus of FIG. 1 with the pusher tube extended to its distal-most position corresponding to the position of the clip pusher after positioning a clip between the jaws, and the channel tube in its proximal position corresponding to open jaws at the distal-most position of the endoscopic section;

FIG. 18 is an elevational cross-sectional view of the handle section of the apparatus of FIG. 1 illustrating the pusher tube in its proximal position corresponding to the clip pusher in position behind the next clip to be advanced and the channel tube in its distal-most position after having closed the jaws of the clamp;

FIG. 19 is an elevational cross-sectional view of the handle of FIG. 1 illustrating the channel tube in locked position after the last clip has been pushed into the jaws of the endoscopic section and the pusher bar has engaged a distal slot in the clip follower, locking the pusher tube in the position shown;

FIG. 20 is a cross-sectional view taken along lines 20—20 of FIG. 17 and illustrating the channel tube and pusher bar;

FIG. 21 is a view taken along lines 21—21 of FIG. 17 illustrating the pusher tube and the channel tube in cross-section;

FIG. 22 is a cross-sectional view taken along lines 22—22 of FIG. 17 illustrating the pusher tube mainspring and the connection between the pusher tube and the pusher bar;

DETAILED DESCRIPTION OF THE PREFERRED EMBODIMENTS

Figure 1:
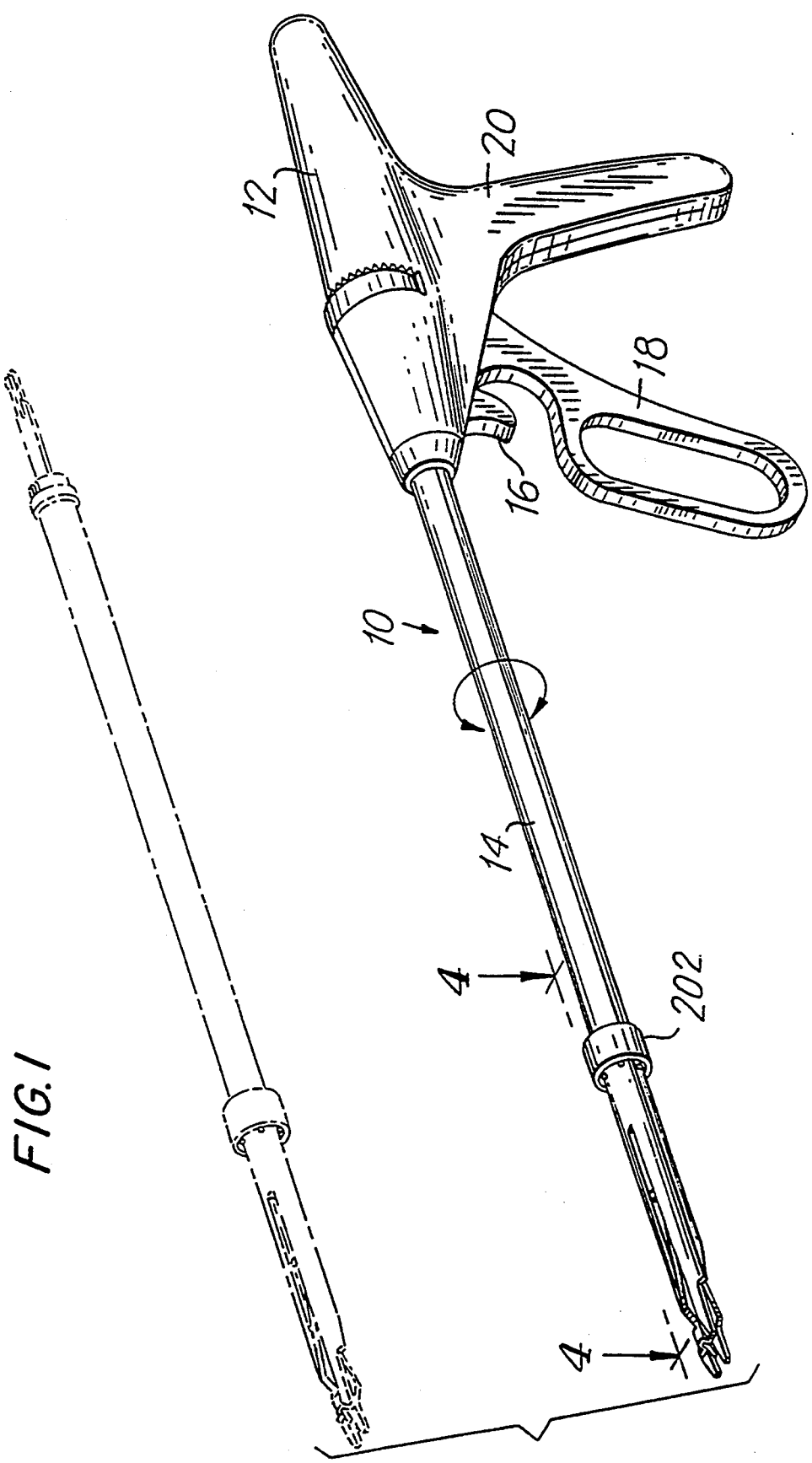
FIG. 1 is a perspective view of the disposable apparatus for placing clips in laparoscopic or endoscopic procedures constructed according to the present invention.

Referring initially to FIG. 1, the apparatus for applying clips in endoscopic and laparoscopic procedures is disclosed in perspective view. The apparatus is preferably constructed as a disposable item of several materials as will be described. Essentially, however, two basic materials are used, i.e., a polycarbonate material such as LEXAN brand plastic material by General Electric Company and stainless steel. Other suitable materials are contemplated.

Briefly, the apparatus 10 includes two main sections. A handle section 12 and an endoscopic section 14 which is distal of the handle section. A clip pushing system which will be described hereinbelow is operative by single finger operative trigger 16 and a clip clamping mechanism is operative by squeezing handle 18 toward hand grip 20 using multiple fingers of the operator. A safety locking device 202 which will be described in detail hereinbelow pertains to the use of the apparatus with a cannula such as a trocar guide tube, which is inserted into an aperture formed by a trocar in the patient's body. As will be seen from the description which follows, device 202 prevents use of the instrument with a cannula of incorrect size.

Referring now to FIGS. 2 and 4–14 in conjunction with FIG. 1, the endoscopic section 14 of the apparatus 10 will now be described. The endoscopic section 14 is preferably housed in a non-removable cartridge formed of upper half section 15 and lower half section 16. Each half section is formed of a material capable of withstanding the stresses applied by the inner working compartments without deformation or compromise of precision. A polycarbonate material such as LEXAN brand material marketed by General Electric Corporation has been found to satisfy the requisite strength and deformation requirements. Other suitable materials may be used. If desired, the cartridge can be constructed to be removable from the handle.

The lower housing half section 16 includes upstanding tabs 18 and the upper housing half section 14 includes correspondingly positioned slots (not shown) which are dimensioned to receive tabs 18 such that the two half sections may be attached by ultrasonic welding techniques. Preferably, the slots are dimensioned to receive the tabs 18 in interference relation to assist securement of the half portions together. Alternatively, the half sections may be adhesively attached. Further, upper half section 15 includes longitudinally extending slots 20 which receive correspondingly dimensioned ribs in the collar of the handle section (to be described) to facilitate rotation of the endoscopic section with the collar.

Referring once again to FIG. 2, a plurality of U-shaped clips 22 are positioned within the housing for movement in the distal direction in preparation for the clamping procedures. The clips are preferably of titanium for use in clipping blood vessels such as arteries. This material avoids the "starburst" effect and facilitates enhanced CT imaging. The clips 22 are aligned in a row as shown, with the leg portions facing distally. A jaw blade 26 is positioned at the distal end and includes a pair of jaws 24 for reception of each clip whereby the jaws are brought together to close the clip about the artery.

Figure 12:
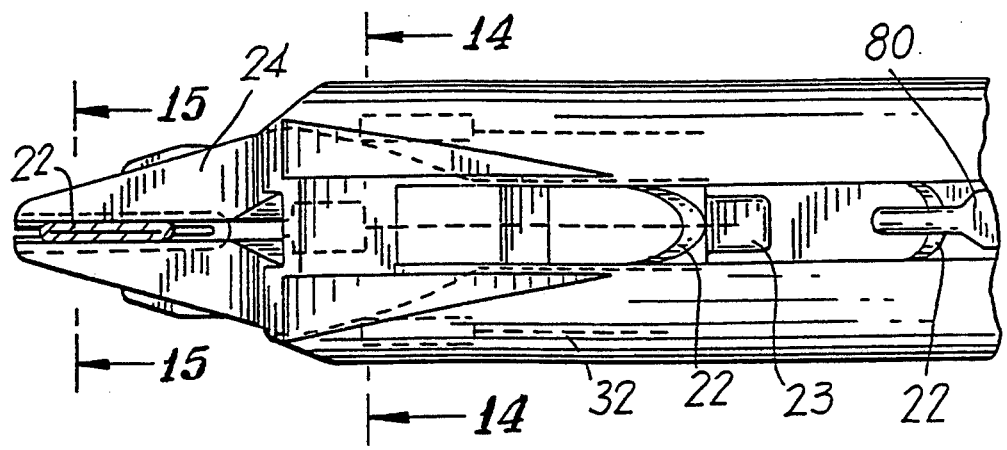
FIG. 12 is a plan view from above of the distal portion of the endoscopic section illustrating a clip positioned within the clamp jaws after clamping is completed about an artery.
Figure 13:
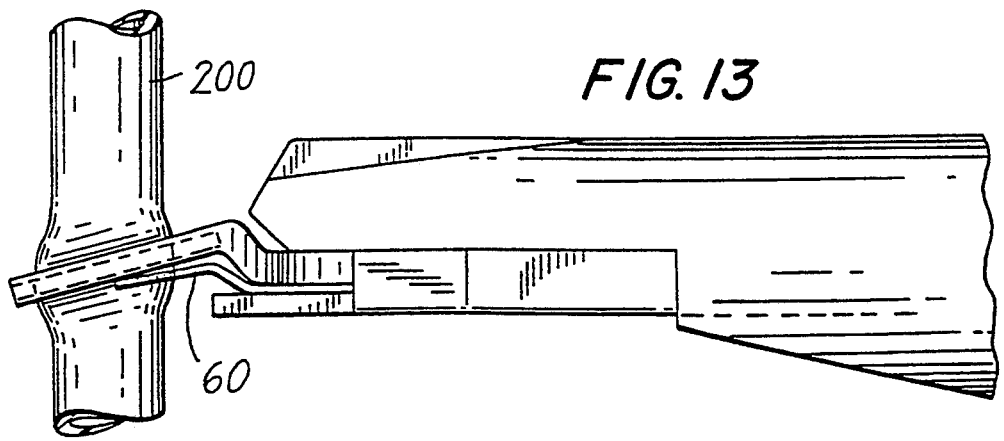
FIG. 13 is a side view thereof.
Figure 14:
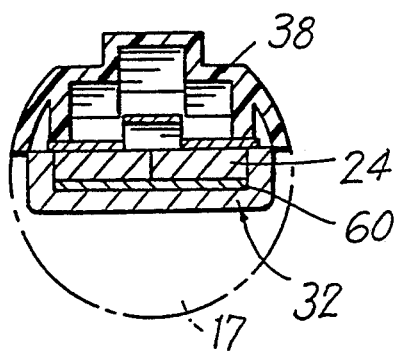
FIG. 14 is a cross-sectional view taken along lines 14—14 of FIG. 12.

The basic objective is to bias the clips toward the distal direction and to sequentially advance each clip into the jaws after the jaws have been positioned about an artery. Thereafter, the jaws are closed and both legs of the "U" shaped clip are brought together to just sufficiently close the artery as shown in FIG. 12.

The jaw blade 26 is fabricated of a material having sufficient resilience such that clamping of the distal pair of jaws 24 toward each other to close a clip therebetween will be followed by return of the jaws to their original position upon release of the clamping forces. Stainless steel has been found to be a preferred material capable not only of withstanding the requisite number of clamping cycles without adverse affect, but also of being suitably sterilized. Furthermore, jaw blade 26 includes three square shaped apertures 28 dimensioned to receive three correspondingly shaped pins 30 molded into the lower body half section 16 of the housing to position the jaw blade 26 with respect to the body.

Figure 2:
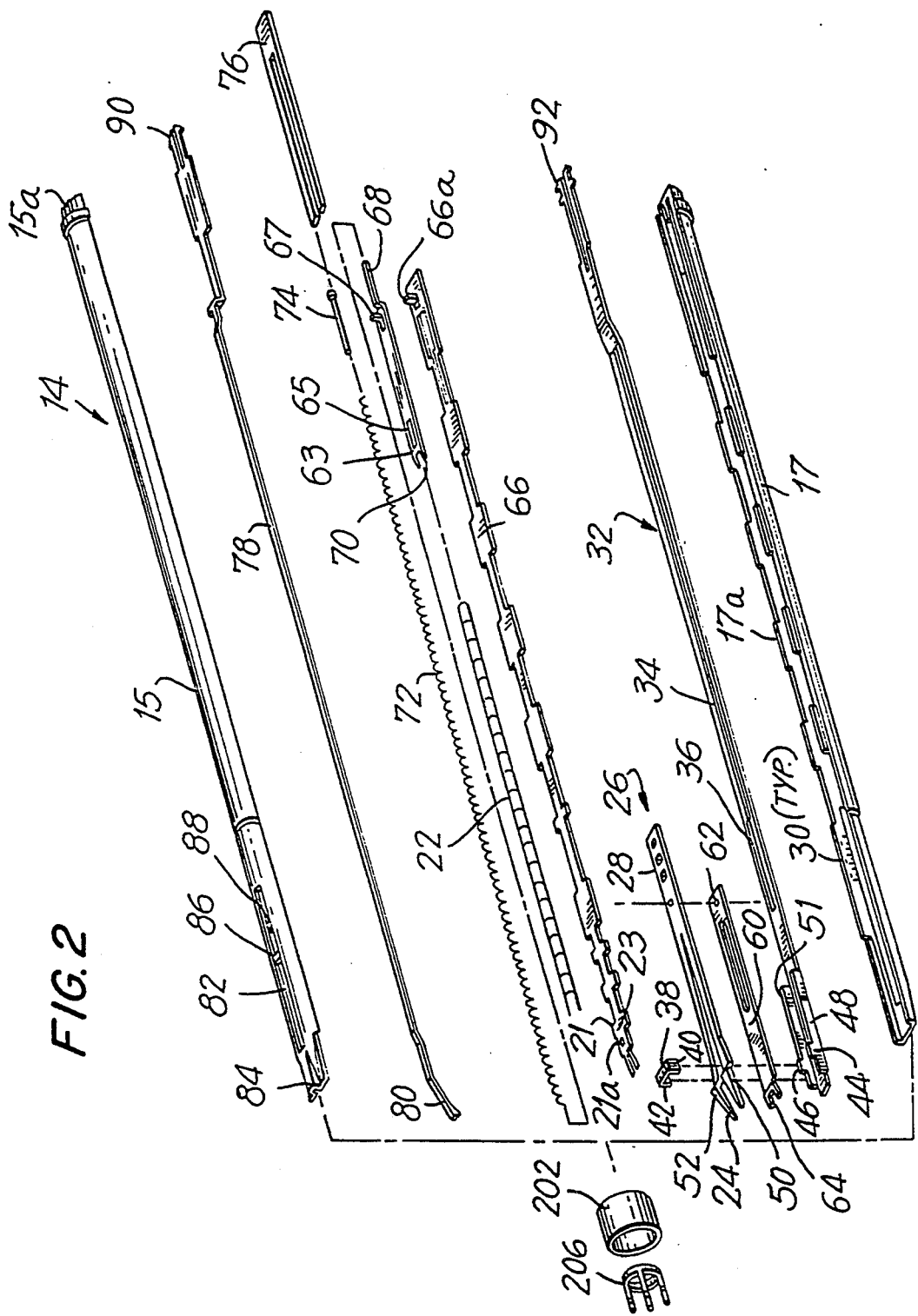
FIG. 2 is a perspective view with parts separated for purposes of illustration of the endoscopic section of the apparatus of FIG. 1.

Referring further to FIG. 2, crimping channel 32 is dimensioned and positioned for slidable movement within the body of the housing and defines elongated slot 34 having a wider portion 36 at the distal end for reception of square pins 30. The width of the slot 34 in distal portion 36 of crimping channel 32 is just sufficient to receive the pins 30 to maintain relative alignment between the jaw blade 26 and the pins 30. A channel bracket 38, also preferably of stainless steel, is positioned atop the jaw blade and defines two downwardly extending side walls 40, 42 positioned to be welded to the distal portions of correspondingly positioned and dimensioned upwardly extending side walls 48, 50 of crimping channel 32. This channel bracket 38 is positioned just distally of upstanding tabs 44, 46. It will be appreciated that the crimping channel 32 forms with channel bracket 38, a rectangular slidable housing surrounding the jaws 24 of jaw blade 26. Moreover, since the jaw members 24 are formed of outwardly tapered side walls 50, 52, movement of the crimping channel 32 in the distal direction will cause inward movement of the jaw members, while movement of the crimping channel in the proximal direction will result in corresponding proximal movement of channel bracket 38 thereby relieving the jaw members 24 of the crimping forces and permitting the jaw members to open.

Figure 15:
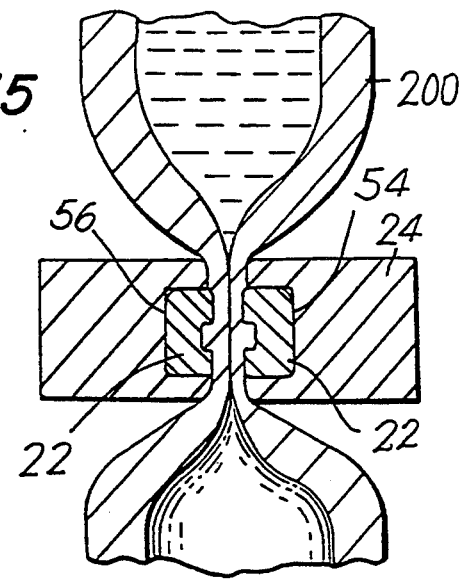
FIG. 15 is a cross-sectional view taken along lines 15—15 of FIG. 12.
Figure 24:
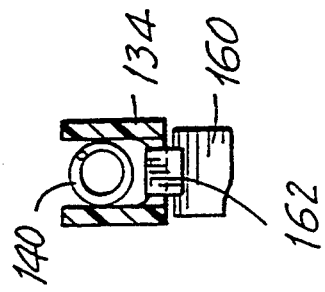
FIG. 24 is a cross-sectional view taken along lines 24—24 of FIG. 17, illustrating the pusher tube and the mainspring.
Figure 25:
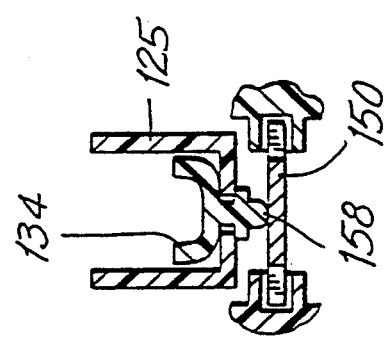
FIG. 25 is a cross-sectional view taken along lines 25—25 of FIG. 17 illustrating release of the channel tube latch plate by the pusher tube.
Figure 23:
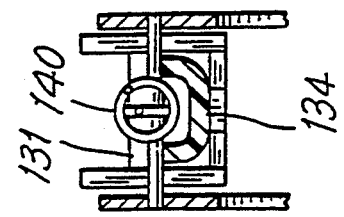
FIG. 23 is a cross-sectional view taken along lines 23—23 of FIG. 17 illustrating the pusher tube and the pusher tube link pin.
Figure 26:
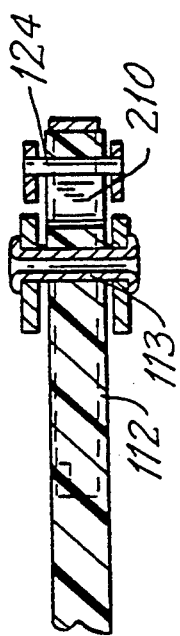
FIG. 26 is a cross-sectional view taken along lines 26—26 of FIG. 17 illustrating the lost motion spring which permits partial clamping of the surgical clips.

Referring now to FIGS. 2 and 15, jaw members 24 include generally longitudinal grooves 54, 56 dimensioned to receive a clip 22 therebetween for clipping a body portion. Tissue stop plate 60 shown in FIG. 2, is positioned between jaw blade 26 and crimping channel 32 and includes aperture 62 at the proximal end portion for reception of an appropriate pin (not shown) which extends through the jaw blade 26 and tissue stop plate 60 to maintain alignment of the jaw blade 26 and the tissue stop plate 60 when these components are welded together. At the distal portion of the tissue stop plate a tab 64 is oriented at approximately the same downward angle as the jaws 24 for alignment therewith and includes an arcuate cut-out portion as shown, dimensioned to snugly receive an artery for locating and positioning the artery in the precise area within the jaw blades as required for applying a clip to the artery with predetermined precision. The tissue stop plate is preferably fabricated of a thin stainless steel sheet material.

Referring further to FIG. 2, cover plate 66 is appropriately dimensioned to rest atop the clip clamping mechanism described hereinabove, and supports the row of clips 22. Proximally of clips 22 is positioned a clip follower 68 which is "U" shaped at the distal end to snugly engage and advance the clips under the action of clip feed spring 72 connected thereto at the distal end and to a pin 74 at the proximal end. Pin 74 is in turn connected to pusher bar support 76 while clip pusher bar 78 is positioned for slidable movement thereon between a proximal position and a distal-most portion. When the next clip 22 is engaged by the distal nose 80 of clip pusher 78, distal movement of the clip pusher 78 advances the clip into the slots 54, 56 of jaws 24 of the jaw blade 26.

Referring again to FIG. 2, upper housing half section 15 includes a longitudinal slot 82 having bridge connections 84, 86, 88 as shown. In position, the clip pusher bar 78 is snaked over bridge 88 and under distal bridges 86 and 84 such that bridge 88 will act as a stop mechanism to prevent the advancement of clip follower 68 when upstanding tab 67 engages bridge 88 as shown in FIG. 5a. This occurs when the last clip 22 has been advanced and crimped thereby permitting the clip follower to advance to its distal-most position under action of spring 72.

Thus by sliding clip pusher bar 78 between the proximal and distal positions, the clip pusher bar may be alternately positioned with nose 80 behind each successive clip, and thereafter advancing the clip into the jaws 24 of jaw blade 26 by a pusher mechanism in handle section 12 which will be described. The connection between the mechanism in the handle 12 is made with the proximal end portion 90 of clip pusher 78 which extends into the handle section. Further, the connection between the appropriate link of handle 12 with the crimping mechanism of jaw blades 24 is made with the proximal end portion 92 of crimping channel 32 as will be described. The precise action of the handle 12 and its inner mechanism is such that proximal force applied to trigger 16 causes clip pusher 78 to push the next clip 22 into the laws 24 while simultaneously releasing the crimping channel 32 to the "ready" position for crimping the clip. Next, the operator squeezes handle 18 toward hand grip 20 which causes crimping channel 32 to move distally to crimp the clip positioned within jaws 24, while simultaneously moving clip pusher 78 proximally in position to push the next clip 22 into the jaws 24. These movements are alternately repeated until the last clip 22 is spent.

Figure 3:
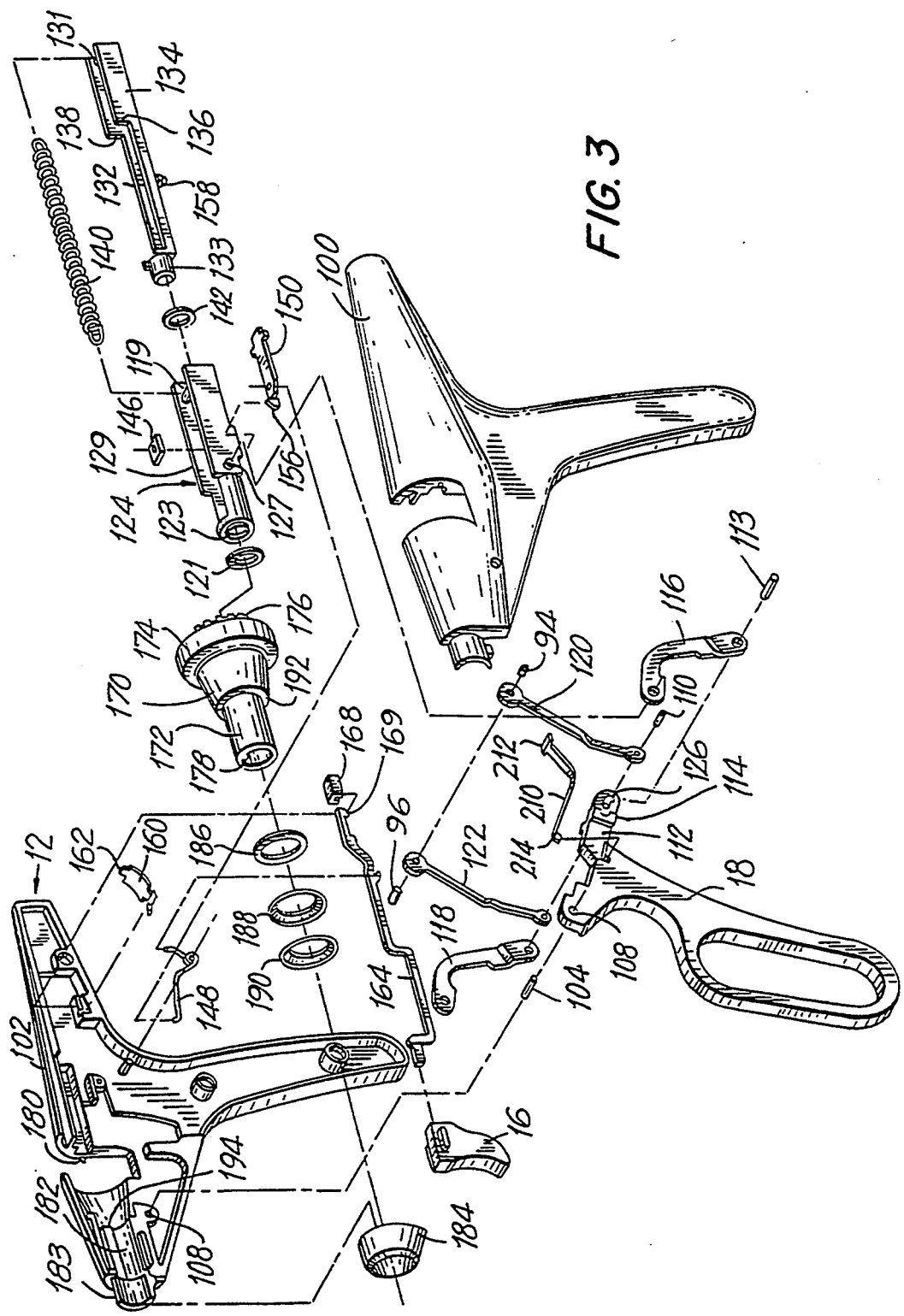
FIG. 3 is a perspective view with parts separated for purposes of illustration of the handle section of the apparatus of FIG. 1 utilized for activating the endoscopic section.

Referring to FIG. 3 the handle section 12 of the apparatus is illustrated with the transmission mechanism for manually activating the endoscopic section described previously, i.e., advancing clips distally and crimping the clips about an artery. The parts of the handle section 12 are separated for convenience of illustration. The handle section 12 includes left body 100 and right body 102. The body parts are fastened together by fasteners such as screws or rivets extending through appropriate bosses. Alternatively, the body parts may be ultrasonically welded or adhesively attached together along their seams or by bosses and transverse rods or pins in engaged relation. The body parts 100, 102 are preferably fabricated of a hard plastic material such as LEXAN Brand polycarbonate material marketed by General Electric Co. Other rigid materials are contemplated. Materials capable of being molded into shape while being able to sustain the forces applied by the transmission mechanism are preferred.

The clip loading and crimping system is divided into two separate systems as described in connection with the endoscopic section. As noted, a first system pushes the clip next in line from a row of clips to a position within a pair of clamping jaws 24 as described in connection with the endoscopic section of the apparatus. The second system closes the pair of jaws 24 around the staple to cause the clip to grip the intended artery, tissue, or other blood vessel, while simultaneously repositioning the clip pusher mechanism to push the clip next in line into position between the jaws. This procedure is repeated alternately and sequentially until all clips are spent.

Referring now to FIGS. 16–19, in conjunction with FIG. 3, the staple pusher and clamping loading mechanism will now be described. Handle 18 is pivotally mounted via aperture 108 on pin 104 extending transversely of the body parts. The handle 18 includes a rearward extension 112 which defines arcuate slot 126 through which pin 110 extends. Pin 113 extends through aperture 114 and functions as a pivot for left channel link 116 and right channel link 118 which extend in a generally forward direction. Rearwardly directed left pusher link 120 and right pusher link 122 are mounted for pivotal motion on pin 110 extending through arcuate slot 126.

At the opposite ends left channel link 116 and right channel link 118 are pivotally mounted to channel tube 124 by pivot pins 127, 129 formed integral therewith and pusher links 120, 122 are connected to transverse pins 94, 96 arranged for slidable movement within the forward cutout portion 132 of pusher tube 134 for engagement with shoulders 136, 138 of the pusher tube when the links are moved in the proximal direction.

Main spring 140 connects channel tube 124 with pusher tube 134 via pins 119, 131, such that the spring is loaded when the tubes are separated by squeezing handle 18 toward handle grip 20 causing distal movement of channel tube 124 and proximal movement of pusher tube 134.

Referring now once again to FIGS. 3 and 16 in conjunction with FIG. 2, it can be seen that pusher tube 134 is connected to clip pusher bar 78 by proximal end tabs 90 which are inserted by squeeze and release action into the distal opening 133 of pusher tube 134 with annular steel pad 142 positioned as an interface between the plastic pusher tube and the steel pusher bar. Similarly, the crimping channel 32 is connected to the channel tube 124 by insertion of the proximal legs 92 into the distal opening 123 of channel tube 124 with annular steel pad 121 positioned as an interface between the plastic channel tube 124 and the steel legs 92. With the connections described, the crimping channel and clip pusher are free to rotate independently of the channel tube and pusher tube as permitted by the rotation of the proximal legs 90 and 92, within the distal opening 133 of pusher tube 134 and opening 123 of channel tube 124.

Referring once again to FIG. 3, latch plate 150 is pivotally mounted and biased upward toward apertured plate 146 in lower wall of channel tube 125 by spring 148 such that tongue 156 enters the aperture of plate 146 when the channel tube 125 is moved to its proximal position. This prevents unwanted forward movement of the channel tube 125 prior to advancing a clip in position within jaw members 24 of jaw plate 26. Release of tongue 156 is accomplished by engagement of the latch plate 150 by pin 158 extending downwardly from pusher tube 134 when pusher tube moves distally under action of mainspring 140 as will be developed further. Similarly, pusher release leaf spring 160 is positioned for entry of tab 162 into a slot 161 in the bottom wall of pusher tube 134 when the tube is moved proximally by pusher links 120, 122 against the force of mainspring 140, permitting the leaf spring 160 to retain the pusher tube in position against the force of the mainspring 140. Release of the pusher release leaf spring 160 is accomplished by proximal movement of release lever 164 via finger activated pusher release button 16 supported at the proximal end by lever support block 168 which slidably moves against the lower wall of pusher tube 134.

In operation, squeezing the handle 18 toward hand grip 20 causes pusher links 120, 122 to pivot and move proximally, resulting in proximal movement of pusher tube 134 by engagement of pins 94, 96 with shoulders 136, 138 of pusher tube 134. Proximal movement of pusher tube 134 continues with pusher release spring 160 continuously biased upwardly until tab 162 enters the slot 161 in the bottom wall of pusher tube 134 thereby retaining pusher tube 134 in position against the bias of mainspring 140. Simultaneously, this action withdraws clip pusher 78 to a position just proximal of the next clip 22 in preparation for pushing the clip distally between the jaw members 24 of jaw blade 26. Retention of the pusher tube in this proximal position by release spring 160 also retains the clip pusher 78 in the corresponding position until the clip next in line is to be pushed into the jaws 24. When this is desired, proximal movement of pusher release button 16 causes proximal movement of release lever 164 and engagement of proximal tip 169 with pusher release spring 160 causing downward movement of the spring and corresponding release of the pusher tube 134. This action causes distal movement of pusher tube 134 and clip pusher 78 with corresponding distal engagement of nose 80 with the next clip 22 thereby positioning the clip into the slots 54, 56 of jaws 24.

Once clip 22 is positioned within jaws 24 of jaw blade 26 squeezing handle 18 proximally toward hand grip 20 causes distal and pivotal movement of channel links 116, 118, resulting in distal movement of channel tube 124 and corresponding distal movement of crimping channel 32. This action causes channel bracket 38 together with crimping channel 32 to engage and squeeze the jaw members 24 of jaw blade 26 thereby crimping the clip 22 positioned therebetween. At the same time, the proximal movement of pusher tube 134 resets clip pusher 78 to a position just proximal of the next clip in readiness for the next clipping operation. Reentry of the tab 162 of pusher release spring 160 into slot 161 of pusher tube 134 retains the pusher 78 in position behind the next clip 22.

Referring further to FIG. 3 in conjunction with FIG. 2, the feature relating to the rotatable endoscopic section will be described. Rotating collar 170 is constructed of the same material as the handle, i.e. preferably a polycarbonate material such as LEXAN brand material. This collar 170 includes a distal cylindrical nose section 172 and a proximal barrel section 174. The proximal face of the barrel section 174 includes a plurality of proximally extending teeth 176 positioned circumferentially about the proximal face of the barrel section and the cylindrical nose section includes an inwardly extending rib 178 at the distal end. In the assembled condition, the cylindrical nose section rests within the cylindrical distal opening 182 of the distal end of the handle and nose piece 184 is fitted over the distal cylindrical end 183 of the handle as shown in FIGS. 16–18. Bearing washer 186 and spring washers 188, 190 are positioned between shoulder 192 of collar 170 and shoulder 194 formed in the handle body to bias the rotatable collar in the proximal direction causing tooth 180 on the handle body to engage the teeth 176 of the collar 170 to thereby fix the rotatable orientation of the collar. When the surgeon desires to change the angular orientation of the endoscopic section, the collar 170 is merely pushed distally to disengage tooth 180 to free the collar and permit rotation relative to the handle body. Such rotation of the collar is clearly permitted by the fact that the cylindrical nose section of the collar is fit snugly within the corresponding cylindrical distal section 182 of the handle. Except when the tooth 180 of the handle body is engaged with teeth 176 of collar 170, the collar is otherwise free to rotate within the handle.

Referring now to FIG. 2 in conjunction with FIGS. 1 and 3, the distal cylindrical section 172 of collar 170 includes a distal cylindrical opening dimensioned to receive the endoscopic cartridge formed of upper half 15 and lower half 16, with distally positioned tooth 178 of collar 170 positioned within longitudinally extending groove 20 of upper cartridge half 15 to cause the cartridge to rotate with the collar 170. Similarly, the proximal legs 90 of clip pusher bar 78 are permitted to rotate within the distal end portion 133 of pusher tube 134 and the proximal legs 92 of the crimping channel 32 are permitted to rotate within the distal end portion 123 of channel tube 124. Thus, the entire endoscopic section may be selectively rotated by the surgeon by simply pushing collar 170 in the distal direction sufficient to disengage tooth 180 on the handle body and by rotating the collar 170 until the endoscopic section reaches the desired angular orientation. Thereafter, by merely releasing the collar the bias of spring washers 190, 188, causes the collar to move proximally, such that tooth 180 on the handle body engages the appropriate teeth 176 on the collar 170 to lock the position of the collar and the endoscopic section. This feature represents a significant advance in endoscopic surgery when it is fully appreciated that the orientation of human tissue or arteries to be clamped vary widely and that selectivity of orientation of the clip is a necessity. Without the above-described feature, the entire apparatus must otherwise be rotated until the proper orientation of the endoscopic section is reached. Such rotation of the entire apparatus during a delicate surgical operation would be prohibitive.

Referring now to FIGS. 12, 13, 14 and 15, the jaws of the clamping section of the apparatus are illustrated. FIG. 12 illustrates the jaws 24 of the apparatus in position after having applied a clip 22 about an artery 98 or other blood vessel to stop the blood flow as illustrated graphically in FIG. 15. As shown in FIG. 15, the jaw members 24 include longitudinally extending grooves 54, 56 which receive clip 22 as the clip is advanced distally by pusher bar 78. It can be seen that at the time the jaw members 24 are clamped together, the nose 80 of pusher bar 78 has been withdrawn proximally to a position proximal of the next clip 22 and is not permitted to advance in the distal direction until the surgeon pulls pusher release button 16 in the proximal direction to release the clip pusher mechanism described previously. Tab 23 prevents the next clip from moving proximally with the pusher bar when the pusher bar returns to a position proximal of the next clip for the sequence. Also, prior to release of the pusher bar for distal movement, fingers 21 upstanding from track 66 prevent distal movement of the next clip preventing the clip from falling out through the jaws. In addition, it is significant to note that once the jaw members 24 are released from their clamped condition shown in FIG. 12, by release of handle 18, clamping of the jaw members 24 may not be repeated until the pusher release button 16 has been depressed to deliver the next clip between the jaws 24. Such clamping action is prevented by the position of tongue 156 within the aperture of plate 146 in the bottom wall of channel tube 124 under the upward bias of spring 148. This position prevents distal movement of the channel tube 124 until the tongue 156 is released from the aperture of plate 146 by engagement of downwardly extending finger 158 of pusher tube 134 with latch plate 150 when pusher tube 134 is caused to advance distally by releasing pusher release button 16.

The release action on tongue 156 is shown more clearly in FIG. 17 which illustrates the handle with the pusher tube 134 in the distal-most position after pusher release button 16 has been depressed to advance the next clip into the jaw members 24 of jaw blade 26. It can be seen clearly in FIG. 17 that finger 158 has engaged latch plate 150 pivoting the latch plate downwardly in the counter clockwise direction against the upward bias of latch spring 148. It will similarly be appreciated that the proximal movement of pusher tube 134 during the squeezing action of handle 18 and jaw members 24 will continue until the tab 162 of the upwardly biased pusher release spring 160 engages the slot in the bottom wall of the proximal section of pusher tube 134 thereby causing the pusher tube to be locked in position corresponding to the nose 80 of pusher bar 78 being positioned just proximal of the next clip 22 for the next clip advancing step as described hereinabove. It can be appreciated readily that this safety feature avoids the possibility of squeezing the jaw members 24 about an artery or other tissue with no clip positioned therebetween. Thus, the only time in the sequence of operation that the jaws can be squeezed is after the advancement of a clip 22 therebetween.

Referring now to FIGS. 4–11, the inner mechanism and function of the distal portion of the endoscopic section are illustrated. In FIG. 4 a plan view from above, is shown of the distal portion of the endoscopic section, illustrating the jaw members 24 and the nose 80 of pusher bar 78 in position to advance the clip 22 into the jaw members. At this time, the row of clips 22 are advanced to their distal-most positions under bias action of clip feed spring 72 between anchor shaft 74 on pusher bar support 76 and pin 71 on clip follower 68 shown in FIG. 2. FIG. 5 is a cross-sectional view taken along lines 5—5 of FIG. 4 illustrating the clip 22 and the nose 80 of pusher bar 78 in position just proximally thereof. The view of the nose 80 of pusher bar 78 shown in dotted lines is intended to illustrate the proximal-most position of the nose 80 of pusher bar 78 as represented by the last portion of the squeezing motion of handle 18 toward hand grip 20 thus establishing with certainty, that the nose 80 of clip pusher 78 is in fact positioned proximally of the next clip 22 after the handle 18 is released and the nose 80 of pusher bar 78 is permitted to move distally a small distance as shown behind clip 22 as represented by relaxation of the combined tolerance build-up of the components interacting with each other. Escapement means in the form of upstanding tabs 21 in cover plate 66 prevent the next clip 22 from distal movement before it has been advanced distally by the pusher bar 78. Also these tabs engage slot 65 in clip follower 68 to assist maintaining the clip follower in the distal most position when the last clip is spent. In addition, they assist forward movement of each clip into the jaws by lifting the legs of the clip prior to movement onto arch 21a. Arch 21a assists proper orientation of the clip entering the jaws. Tab 23 prevents proximal movement of clip 22 once it has been advanced distally by nose 80, i.e. the proximal return movement of nose 80 does not move clip proximally (by friction) along with the nose.

FIG. 5a illustrates still another significant feature of the present invention which prevents further distal advancement of the clip pusher 78 after the last clip 22 has been advanced distally into the jaws 24 and clamped about an artery. In particular, the proximal portion of clip follower 68 includes upstanding tab 67 which is positioned and dimensioned to engage bridge 88 on upper cartridge half 15 when clip follower 68 assumes the distal-most position shown in FIG. 5a under bias of spring 72. This position is assumed by clip follower 68 after the last clip has been advanced distally into the jaws 24. Thus, the engagement of upstanding tab 67 with bridge 88 prevents further distal movement of the clip follower at this stage. Furthermore, as shown in FIG. 5a, the distal position of clip follower 68 results in slot 65 now assuming 1B distal-most position such that nose 80 of clip pusher bar 78 may drop into slot 65 thus preventing further distal movement of the pusher bar 78 after the last clip has been spent. This is a further safety feature of the invention in that the apparatus is inactivated after the last clip is spent, thus avoiding the possibility of the surgeon clamping the jaws 24 about an artery with no clip in position. Upstanding tabs 23 in cover plate 66 also engage bridge 63 in clip follower 68 to maintain the distal position of the follower. FIG. 5b is a cross-sectional view taken along lines 5a—5a of FIG. 5 illustrating the clip follower 68 and the clip cover plate 66 in the position shown in FIG. 5a.

Referring now to FIG. 6, a plan view from above similar to FIG. 4 is shown of the distal portion of the endoscopic section with clip 22 shown in FIG. 5 now advanced distally to a position within the jaws 24 by nose 80 of clip pusher 78. FIG. 7 is a cross-sectional view taken along lines 7—7 of FIG. 6 illustrating the clip 22 and clip pusher bar 78 in the distally advanced position after advancing clip 22 into the jaws 24.

Referring now to FIG. 8 there is shown a cross-sectional view taken along lines 8—8 of FIG. 6 which illustrates the safety locking feature of the invention. This safety locking feature prevents use of the present endoscopic clip applier with a cannula of incorrect size. In particular, it can be seen that the safety device 202 includes housing 204 having locking collar 206 retained in place in the housing by interference fit or adhesive. A plurality of locking fingers 208 are positioned circumferentially about the collar and are constructed of a resilient material which causes their arcuate bent end portions 210 to become locked into position within a circumferential groove 212 formed in the cartridge halves 15 and 16. This longitudinal movement of the locking collar 206 relative to the endoscopic section is prevented unless the bent end portions 210 of fingers 208 are lifted upwardly out of the groove 212. In endoscopic surgical procedures, a cannula in the form of a trocar guide tube is generally positioned within the body wall and extends into the peritoneal cavity which has been insufflated by a gas to protect the body organs. The trocar guide tube normally includes a valve device to maintain the gas under pressure and camming devices of appropriate size and shape to disengage fingers 208 from groove 212. Thus, when the endoscopic section of an instrument is inserted into the trocar guide tube it is necessary to use the correct size guide tube for the endoscopic device. The endoscopic section preferably contains a small quantity of silicone grease with the housing to prevent leakage of gas through the housing.

Referring to FIG. 8, an exemplary part of an entry portion 209 of a trocar guide tube is shown with remaining parts broken away for illustrative purposes. Entry wall 209 of the trocar guide tube is shown with a plurality of camming members 211 configured, dimensioned and positioned to simultaneously lift fingers 206 out of groove 210 to release the safety locking device 202 and permit it to slide proximally along the endoscopic section. Only one camming member 211 is shown for convenience.

When the endoscopic section 12 of the present invention is inserted into the trocar guide tube, if the diameter of the guide tube is excessive, distal movement of the endoscopic section will be prevented by the engagement with collar 202. If the diameter of the trocar guide tube is too small, distal movement of the endoscopic section will be prevented by engagement of the fingers 208 with the guide tube. However, when the trocar guide tube is the correct size and shape, the fingers 206 will be lifted simultaneously out of groove 212 by camming members 211 and collar 202 will readily be permitted to slide in the proximal direction along the endoscopic cartridge thereby permitting insertion of the endoscopic section into the guide tube without loss of gas from the peritoneal cavity. Other appropriate seals are included in the trocar guide tube. The safety locking collar 202 shown is similar to the safety locking disclosed in co-pending U.S. parent patent application Ser. No. 07/479,375, filed Feb. 13, 1990, the disclosure of which is incorporated by reference herein and made a part of this disclosure.

FIG. 9 is a cross-sectional view taken along lines 9—9 of FIG. 6, illustrating the crimping channel 32, the tissue stop 64, clip 22, pusher bar 78 and jaws 24, and cover plate (or clip track) 66.

Figure 10:
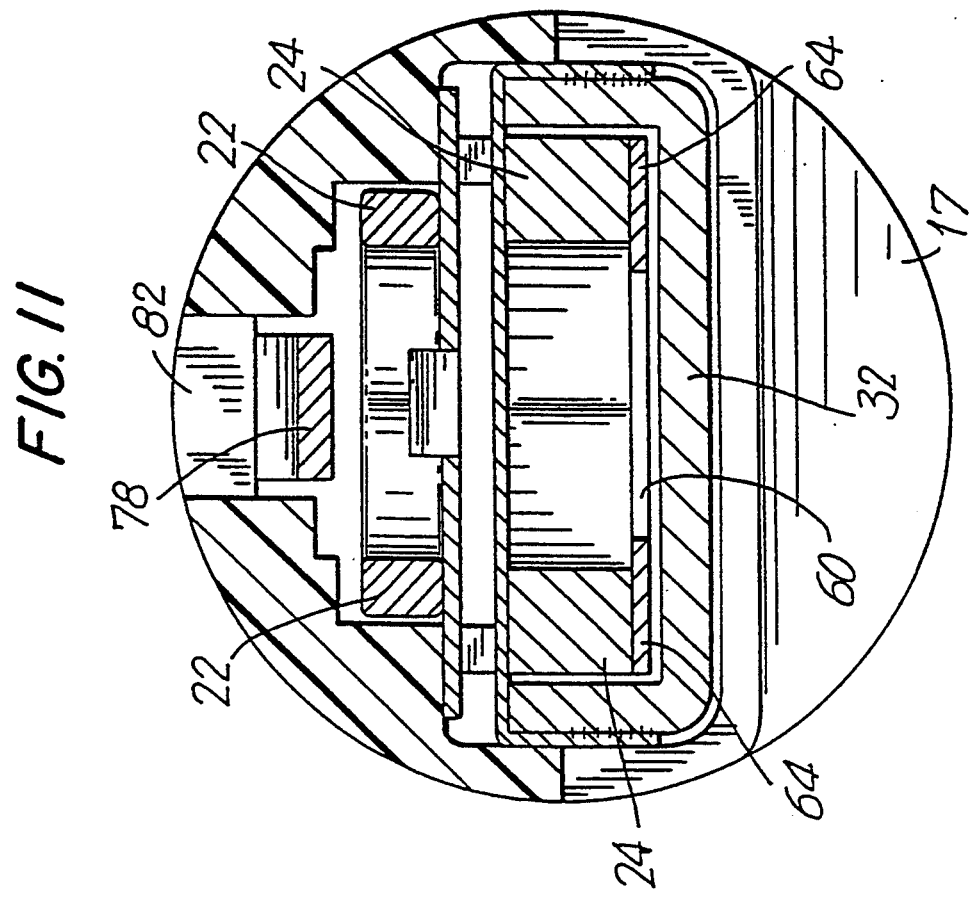
FIG. 10 is a cross-sectional view taken along lines 10—10 of FIG. 6.
Figure 11:
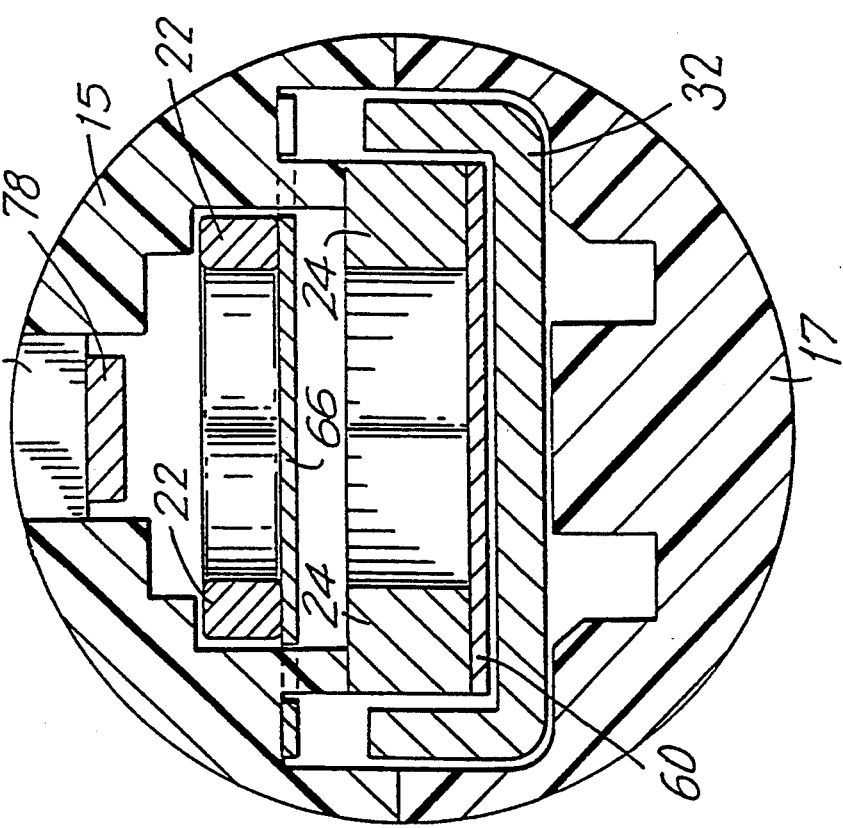
FIG. 11 is a cross-sectional view taken along lines 11—11 of FIG. 6.

FIG. 10 is a similar cross-sectional view taken along lines 10—10 of FIG. 6 illustrating the clip advancing components. FIG. 11 is a cross-sectional view similar to FIG. 10 illustrating the clip advancing mechanism distal of the cross-section shown in FIG. 10.

Referring now to FIGS. 16–19, the inner clip advancing and jaw squeezing mechanism is shown in various stages of the operation. FIG. 16 is an elevational cross-sectional view of the handle 18 of the apparatus, illustrating the pusher tube 134 in the proximal-most position corresponding to the position of the pusher bar 78 shown in FIG. 5, i.e. with the nose 80 just proximal of the next clip 22 in readiness to activate the clip distally into the jaws 24. Additionally, with pusher tube in the proximal position, downwardly extending finger 158 has moved out of engagement with latch 150 thereby permitting tongue 156 to enter the aperture of channel latch plate 146 thus preventing any distal movement of channel tube 124. This condition locks handle 18 in the distal position whereby squeezing the handle toward hand grip 20 is prevented.

Referring now to FIG. 17, there is shown a cross-sectional view of the handle 18 of the apparatus with the pusher tube in the distal-most position corresponding to the position of pusher bar 78 as shown in FIG. 7, i.e. with the clip 22 advanced distally into the jaws 24 of jaw blade 26. As can be seen further in FIG. 17, the distal position of pusher tube 134 has now resulted in release of tongue 156 of latch plate 150 from the aperture of channel latch plate 146 in the bottom wall of channel tube 124 thereby permitting advancement of channel tube 124 and crimping channel 32 distally to squeeze jaws 24 in conjunction with channel bracket 38.

Referring now to FIG. 18, a cross-sectional view of the handle 18 is shown after the crimping action has taken place on clip 22 positioned within jaws 24 shown in FIGS. 16 and 7. The position of the components shown in FIG. 18 corresponds to the position of the jaws shown in FIGS. 12–15, i.e., in the clamped position about clip 22. In the cross-section shown in FIG. 18, the pusher tube 134 in the proximal-most position and the channel tube is in the distal-most position such that crimping channel 32 and channel bracket 40 are in the distal-most position shown in FIGS. 12–15.

Referring to FIG. 19 a cross-sectional view of the handle 18 is shown after the last clip 22 has been spent, i.e. corresponding to the position of the clip follower 68 shown in FIG. 5a. As noted hereinabove, the clip follower 68 of the endoscopic section is prevented from moving further distally by interaction with bridge 88 formed in upper cartridge half section 15. Additionally as noted, it can be seen in FIG. 5a that clip follower 68 defines slot 65 at the distal portion which is bounded on the distal end by a bridge 63 which is positioned to engage the nose 80 of pusher bar 78 when clip follower 68 has advanced to the distal-most position shown in FIG. 5a, i.e. after the last clip has been spent. In this position, the clip follower is now sufficiently distal to engage the nose 80 of clip pusher bar 78 which is biased downwardly by the configuration of pusher bar 78 and by the resilient properties of the material from which the pusher bar is fabricated, i.e. stainless steel. This engagement with bridge 63 prevents further distal movement of clip pusher bar 78 and correspondingly of pusher tube 134. By preventing pusher tube 134 from distal movement with channel tube 124 locked in its proximal position by tongue 156 of latch plate 150, further squeezing action of handle 18 toward hand grip 20 is also prevented. This locking action correspondingly prevents distal movement of crimping channel 32. As shown in FIG. 19, pusher release button is depressed but full distal movement of pusher tube 134 is prevented by the engagement of nose 80 of pusher bar 78 with bridge 63 of clip follower. Only a small distal movement is permitted as seen by the position of slot 161 in pusher tube 134 relative to the position of pusher release spring 160. This locked position of pusher tube 134 also serves to prevent downwardly depending finger 158 of pusher tube 134 from distal movement sufficient to release tongue 156 of latch plate 150 from channel tube 124 as shown. Thus, the crimping mechanism is inactivated for safety purposes.

This feature is extremely significant in disabling the apparatus from squeezing jaws 24 of the jaw blade 26 on an artery alone, i.e. with no clip positioned therebetween. Further, all movement of the clip advance mechanism is now prevented after the last clip has been spent. At this stage, the entire instrument is considered disposable and may be disposed of in accordance with correct approved disposal procedures.

Referring once again to FIG. 3 in conjunction with FIGS. 16–19, the lost motion spring 210 is shown having transverse arms 212 and tab 214. Spring 210 provides bias force on pusher links 120, 122 such that squeezing action on handle 18 maximizes proximal movement of pusher tube 134. Thus, partially closing the jaws 24 of jaw blade 26 will cause pusher tube 134 to move sufficiently proximal to make certain that pusher bar 78 has moved proximally of the next clip 22. Without such movement it may be possible for the surgeon to squeeze the jaws, not fully appreciating that the pusher bar 78 has not moved to a position proximal of the next clip 22. This proximal movement of the pusher bar transmission is thus assisted by lost motion spring 210 which maximizes the repositioning movement of the pusher bar 78 behind the next clip whether the jaws are squeezed fully or partially. In particular, the proximal bias provided by spring 210 on pusher links 120, 122 maximizes the movement of pusher tube 134 in relation to the movement of handle 18 by maintaining pusher links 120, 122 in their proximal-most positions prior to squeezing the handle 18. This maximum proximal movement of pusher links 120, 122 in turn results in proximal movement of pusher tube sufficient to engage tongue 162 of release spring 160 thus making certain that pusher bar 178 is repositioned sufficiently proximally to advance the next clip 22 into the jaw members 24.

What is claimed is:

1. In combination:
   (a) an endoscopic clip applier having an elongated shaft portion which is adapted to be inserted into a trocar guide tube, said elongated shaft portion including:

(i) a clip track for storing a plurality of surgical clips;

(ii) a clip pusher adjacent to and movable with respect to said clip track for individually advancing said surgical clips to clip closing jaws positioned at the distal end of said elongated shaft portion;

(iii) a channel having a distal portion which at least partially surrounds said clip closing jaws for camming said clip closing jaws to form a clip positioned therewithin;

(iv) a gaseous seal means surrounding at least a portion of said clip pusher and said channel for inhibiting the flow of gases through said elongated shaft portion;

(b) a safety device comprising a collar configured and dimensioned to be disposed on the elongated shaft portion and locking means disposed on said collar for releasably engaging said elongated shaft portion; and (c) a trocar guide tube including release means releasing said locking means from engagement with said elongated shaft portion by camming said locking means away from said elongated shaft portion.

* * * * *